United States Patent
Choi et al.

(10) Patent No.: US 11,950,770 B1
(45) Date of Patent: Apr. 9, 2024

(54) MULTI-PORTAL SPLIT CANNULAS, ENDOSCOPIC HEMOSTATIC DISPENSERS AND SURGICAL TOOLS

(71) Applicant: Amplify Surgical, Inc., Irvine, CA (US)

(72) Inventors: Andy Wonyong Choi, Irvine, CA (US); Dong-Hwa Heo, Seoul (KR)

(73) Assignee: Amplify Surgical, Inc., Irvine, CA (US)

( * ) Notice: Subject to any disclaimer, the term of this patent is extended or adjusted under 35 U.S.C. 154(b) by 0 days.

(21) Appl. No.: 18/073,364

(22) Filed: Dec. 1, 2022

(51) Int. Cl.
*A61B 17/00* (2006.01)
*A61B 17/02* (2006.01)

(52) U.S. Cl.
CPC .... *A61B 17/00234* (2013.01); *A61B 17/0218* (2013.01); *A61B 2017/00238* (2013.01)

(58) Field of Classification Search
CPC .......................... A61B 17/3421; A61B 17/7074
See application file for complete search history.

(56) References Cited

U.S. PATENT DOCUMENTS

| | | |
|---|---|---|
| 3,486,505 A | 12/1969 | Morrison |
| 5,171,279 A | 12/1992 | Mathews |
| 5,390,683 A | 2/1995 | Pisharodi |
| 5,437,637 A | 8/1995 | Lieber et al. |
| 5,690,222 A | 11/1997 | Peters |
| 5,762,629 A | 6/1998 | Kambin |
| 5,782,832 A | 7/1998 | Larsen et al. |
| 5,846,182 A | 12/1998 | Wolcott |
| 5,888,223 A | 3/1999 | Bray |
| 6,126,689 A | 10/2000 | Brett |
| 6,162,170 A | 12/2000 | Foley et al. |
| 6,348,058 B1 | 2/2002 | Melkent et al. |
| 6,409,766 B1 | 6/2002 | Brett |

(Continued)

FOREIGN PATENT DOCUMENTS

| | | |
|---|---|---|
| CN | 105636555 A | 6/2016 |
| EP | 3016617 A2 | 5/2016 |

(Continued)

OTHER PUBLICATIONS

Choi, Chang Myong et al. "How I do it? Biportal endoscopic spinal surgery (BESS) for treatment of lumbar spinal stenosis." Acta Neurochir (2016) 158:459-463; published Jan. 18, 2016.

(Continued)

*Primary Examiner* — Andrew Yang
(74) *Attorney, Agent, or Firm* — Perkins Coie LLP

(57) ABSTRACT

A multi-portal method for treating a subject's spine includes distracting adjacent vertebrae using a distraction instrument positioned at a first entrance along the subject to enlarge an intervertebral space between the adjacent vertebrae. An interbody fusion implant can be delivered into the enlarged intervertebral space. The interbody fusion implant can be positioned directly between vertebral bodies of the adjacent vertebrae while endoscopically viewing the interbody fusion implant using an endoscopic instrument. The patient's spine can be visualized using endoscopic techniques to view, for example, the spine, tissue, instruments and implants before, during, and after implantation, or the like. The visualization can help a physician throughout the surgical procedure to improve patient outcome.

29 Claims, 13 Drawing Sheets

(56) References Cited

U.S. PATENT DOCUMENTS

| | | |
|---|---|---|
| 6,641,614 B1 | 11/2003 | Wagner et al. |
| 6,723,126 B1 | 4/2004 | Berry |
| 6,969,392 B2 | 11/2005 | Gitis et al. |
| 7,083,650 B2 | 8/2006 | Moskowitz et al. |
| 7,087,055 B2 | 8/2006 | Lim et al. |
| 7,731,751 B2 | 6/2010 | Butler et al. |
| 7,922,729 B2 | 4/2011 | Michelson |
| RE42,525 E | 7/2011 | Simonson |
| 8,016,767 B2 | 9/2011 | Miles et al. |
| 8,062,375 B2 | 11/2011 | Glerum et al. |
| 8,353,963 B2 | 1/2013 | Glerum |
| 8,382,842 B2 | 2/2013 | Greenhalgh et al. |
| 8,394,145 B2 | 3/2013 | Weiman |
| 8,398,713 B2 | 3/2013 | Weiman |
| 8,425,613 B2 | 4/2013 | Theofilos |
| 8,435,298 B2 | 5/2013 | Weiman |
| 8,491,659 B2 | 7/2013 | Weiman |
| 8,512,407 B2 | 8/2013 | Butler et al. |
| 8,518,120 B2 | 8/2013 | Glerum et al. |
| 8,556,979 B2 | 10/2013 | Weiman et al. |
| 8,568,317 B1 | 10/2013 | Gharib et al. |
| 8,632,594 B2 | 1/2014 | Williams et al. |
| 8,632,595 B2 | 1/2014 | Weiman |
| 8,679,183 B2 | 3/2014 | Glerum et al. |
| 8,685,098 B2 | 4/2014 | Glerum et al. |
| 8,709,086 B2 | 4/2014 | Glerum |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,926,704 B2 | 1/2015 | Glerum et al. |
| 8,940,048 B2 | 1/2015 | Butler et al. |
| 8,986,386 B2 | 3/2015 | Oglaza et al. |
| 9,034,041 B2 | 5/2015 | Wolters et al. |
| 9,039,771 B2 | 5/2015 | Glerum et al. |
| 9,044,342 B2 | 6/2015 | Perloff et al. |
| 9,078,769 B2 | 7/2015 | Farin |
| 9,119,730 B2 | 9/2015 | Glerum et al. |
| 9,125,757 B2 | 9/2015 | Weiman |
| 9,149,367 B2 | 10/2015 | Davenport et al. |
| 9,155,628 B2 | 10/2015 | Glerum et al. |
| 9,186,258 B2 | 11/2015 | Davenport et al. |
| 9,198,765 B1 | 12/2015 | Pimenta |
| 9,198,772 B2 | 12/2015 | Weiman |
| 9,204,972 B2 | 12/2015 | Weiman et al. |
| 9,204,974 B2 | 12/2015 | Glerum et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,271,843 B2 | 3/2016 | Fabian et al. |
| 9,278,008 B2 | 3/2016 | Perloff et al. |
| 9,283,092 B2 | 3/2016 | Siegal et al. |
| 9,295,562 B2 | 3/2016 | Lechmann et al. |
| 9,308,099 B2 | 4/2016 | Triplett et al. |
| 9,320,613 B2 | 4/2016 | Dmuschewsky |
| 9,351,848 B2 | 5/2016 | Glerum et al. |
| 9,358,126 B2 | 6/2016 | Glerum et al. |
| 9,358,128 B2 | 6/2016 | Glerum et al. |
| 9,358,129 B2 | 6/2016 | Weiman |
| 9,370,434 B2 | 6/2016 | Weiman |
| 9,402,739 B2 | 8/2016 | Weiman et al. |
| 9,408,708 B2 | 8/2016 | Greenhalgh |
| 9,414,934 B2 | 8/2016 | Cain |
| 9,414,936 B2 | 8/2016 | Miller et al. |
| 9,452,063 B2 | 9/2016 | Glerum et al. |
| 9,456,903 B2 | 10/2016 | Glerum et al. |
| 9,474,623 B2 | 10/2016 | Cain |
| 9,474,625 B2 | 10/2016 | Weiman |
| 9,480,573 B2 | 11/2016 | Perloff et al. |
| 9,480,578 B2 | 11/2016 | Pinto |
| 9,486,325 B2 | 11/2016 | Davenport et al. |
| 9,486,328 B2 | 11/2016 | Jimenez et al. |
| 9,492,283 B2 | 11/2016 | Glerum |
| 9,492,287 B2 | 11/2016 | Glerum et al. |
| 9,492,288 B2 | 11/2016 | Wagner et al. |
| 9,510,954 B2 | 12/2016 | Glerum et al. |
| 9,522,068 B2 | 12/2016 | Goel et al. |
| 9,539,108 B2 | 1/2017 | Glerum et al. |
| 9,545,319 B2 | 1/2017 | Farin |
| 9,554,918 B2 | 1/2017 | Weiman |
| 9,561,116 B2 | 2/2017 | Weiman et al. |
| 9,561,117 B2 | 2/2017 | Lechmann et al. |
| 9,566,168 B2 | 2/2017 | Glerum et al. |
| 9,579,124 B2 | 2/2017 | Gordon et al. |
| 9,579,130 B2 | 2/2017 | Oglaza et al. |
| 9,597,197 B2 | 3/2017 | Lechmann et al. |
| 9,597,200 B2 | 3/2017 | Glerum et al. |
| 9,610,175 B2 | 4/2017 | Barreiro et al. |
| 9,610,176 B1 | 4/2017 | Abdou |
| 9,615,937 B2 | 4/2017 | Barreiro |
| 9,655,744 B1 | 5/2017 | Pimenta |
| 9,888,859 B1 | 2/2018 | Spangler et al. |
| 9,901,457 B2 | 2/2018 | Sack et al. |
| 10,105,238 B2 | 10/2018 | Koch et al. |
| 10,201,431 B2 | 2/2019 | Slater et al. |
| 10,327,912 B1 | 6/2019 | Suddaby |
| 10,945,859 B2 | 3/2021 | Ewer et al. |
| 11,464,648 B2 | 10/2022 | Choi et al. |
| 2002/0107573 A1 | 8/2002 | Steinberg |
| 2002/0143401 A1 | 10/2002 | Michelson |
| 2003/0028251 A1 | 2/2003 | Mathews |
| 2003/0060687 A1 | 3/2003 | Kleeman et al. |
| 2003/0236472 A1 | 12/2003 | Van Hoeck et al. |
| 2006/0149279 A1 | 7/2006 | Mathews |
| 2007/0005088 A1 | 1/2007 | Lehuec et al. |
| 2007/0276406 A1 | 11/2007 | Mahoney et al. |
| 2009/0281551 A1 | 11/2009 | Frey |
| 2010/0331883 A1 | 12/2010 | Schmitz et al. |
| 2011/0184422 A1 | 7/2011 | Mathews |
| 2013/0103103 A1* | 4/2013 | Mire .............. A61B 1/32 606/86 A |
| 2014/0121774 A1 | 5/2014 | Glerum et al. |
| 2014/0249631 A1 | 9/2014 | Weiman |
| 2014/0277497 A1 | 9/2014 | Bennett et al. |
| 2014/0303730 A1 | 10/2014 | Mcguire et al. |
| 2015/0066145 A1 | 3/2015 | Rogers et al. |
| 2015/0265320 A1 | 9/2015 | Hynes et al. |
| 2015/0342586 A1 | 12/2015 | Lim et al. |
| 2016/0051373 A1 | 2/2016 | Faulhaber |
| 2016/0128846 A1 | 5/2016 | Voellmicke |
| 2016/0199194 A1 | 7/2016 | Slater et al. |
| 2016/0270772 A1 | 9/2016 | Beale et al. |
| 2016/0310291 A1 | 10/2016 | Greenhalgh |
| 2017/0042695 A1 | 2/2017 | Foley et al. |
| 2017/0056200 A1 | 3/2017 | Koch et al. |
| 2017/0065269 A1 | 3/2017 | Thommen et al. |
| 2017/0105845 A1 | 4/2017 | Glerum et al. |
| 2019/0142407 A1 | 5/2019 | Jung et al. |
| 2019/0142408 A1 | 5/2019 | Jung et al. |
| 2019/0209154 A1 | 7/2019 | Richter et al. |
| 2020/0015925 A1 | 1/2020 | Scheib |
| 2020/0107824 A1 | 4/2020 | Fleischer |
| 2020/0383675 A1 | 12/2020 | Jung |
| 2021/0068863 A1 | 3/2021 | Choi et al. |
| 2022/0175418 A1* | 6/2022 | Ebersole ............ A61B 17/3423 |

FOREIGN PATENT DOCUMENTS

| | | |
|---|---|---|
| EP | 3038565 A1 | 7/2016 |
| JP | 6096282 B2 | 2/2017 |
| WO | 2013052807 A2 | 4/2013 |
| WO | 2013109346 A1 | 7/2013 |
| WO | 2013173767 A1 | 11/2013 |
| WO | 2014151162 A1 | 9/2014 |
| WO | 2014164625 A1 | 10/2014 |
| WO | 2017015165 A1 | 1/2017 |
| WO | 2017027277 A1 | 2/2017 |
| WO | 2017035155 A1 | 3/2017 |

(56) References Cited

FOREIGN PATENT DOCUMENTS

| WO | 2017051416 A1 | 3/2017 |
| WO | 2021050577 A1 | 3/2021 |

OTHER PUBLICATIONS

Eum, Jin Hwa et al. "Percutaneous biportal endoscopic decompression for lumbar spinal stenosis: a technical note and preliminary clinical results." J Neurosurg Spine 24:602-607, Apr. 2016; published online Jan. 1, 2016.

Innovasive Inc. "Innovasive DualX LLIP expanding IBFD Product Information and Instructions for Use." May 2018, 2 pages.

International Bureau, Written Opinion, PCT Patent Application PCT/US2016/048222 filed Aug. 23, 2016; dated Mar. 2, 2017, 4 pages.

ISA, International Search Report and Written Opinion, PCT Patent Application PCT/US2020/049982, dated Jan. 26, 2021, 21 pages.

Kim, Jin-Sung et al., "Endoscope-assisted oblique lumbar interbody fusion for the treatment of cauda equina syndrome: a technical note." Eur Spine J (2017) 26:397-403.

\* cited by examiner

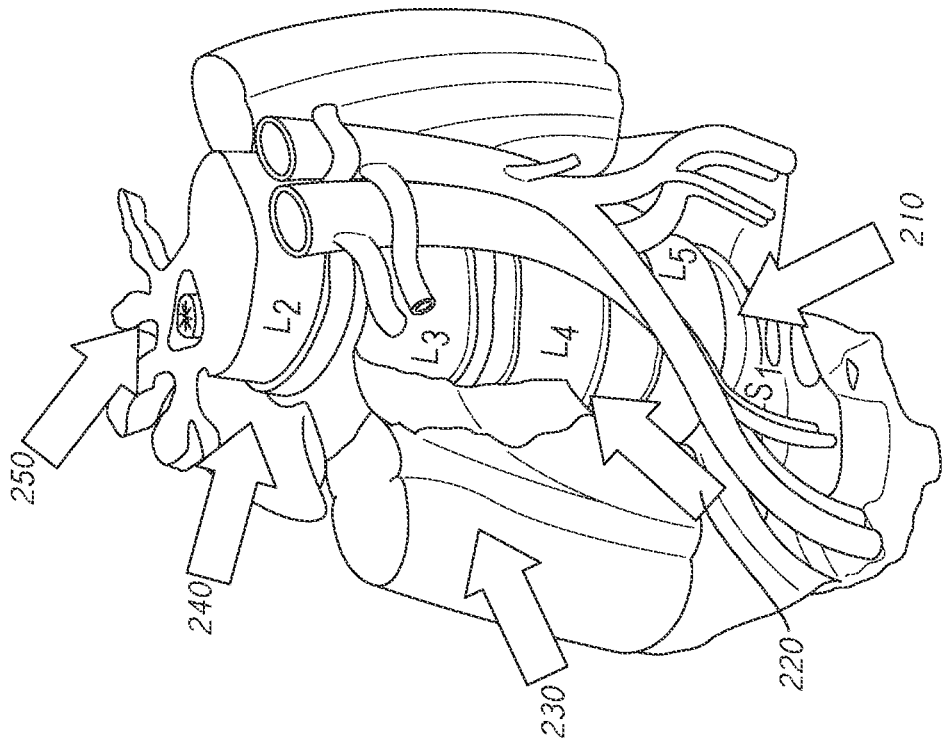
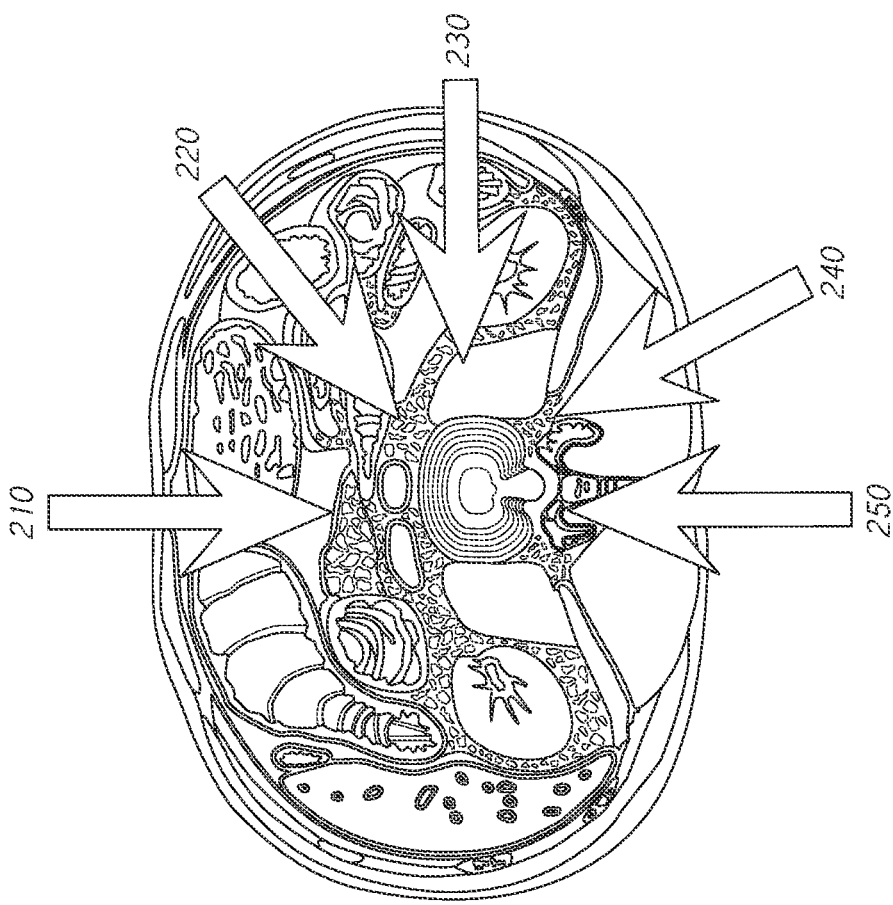
FIG. 2B
FIG. 2A

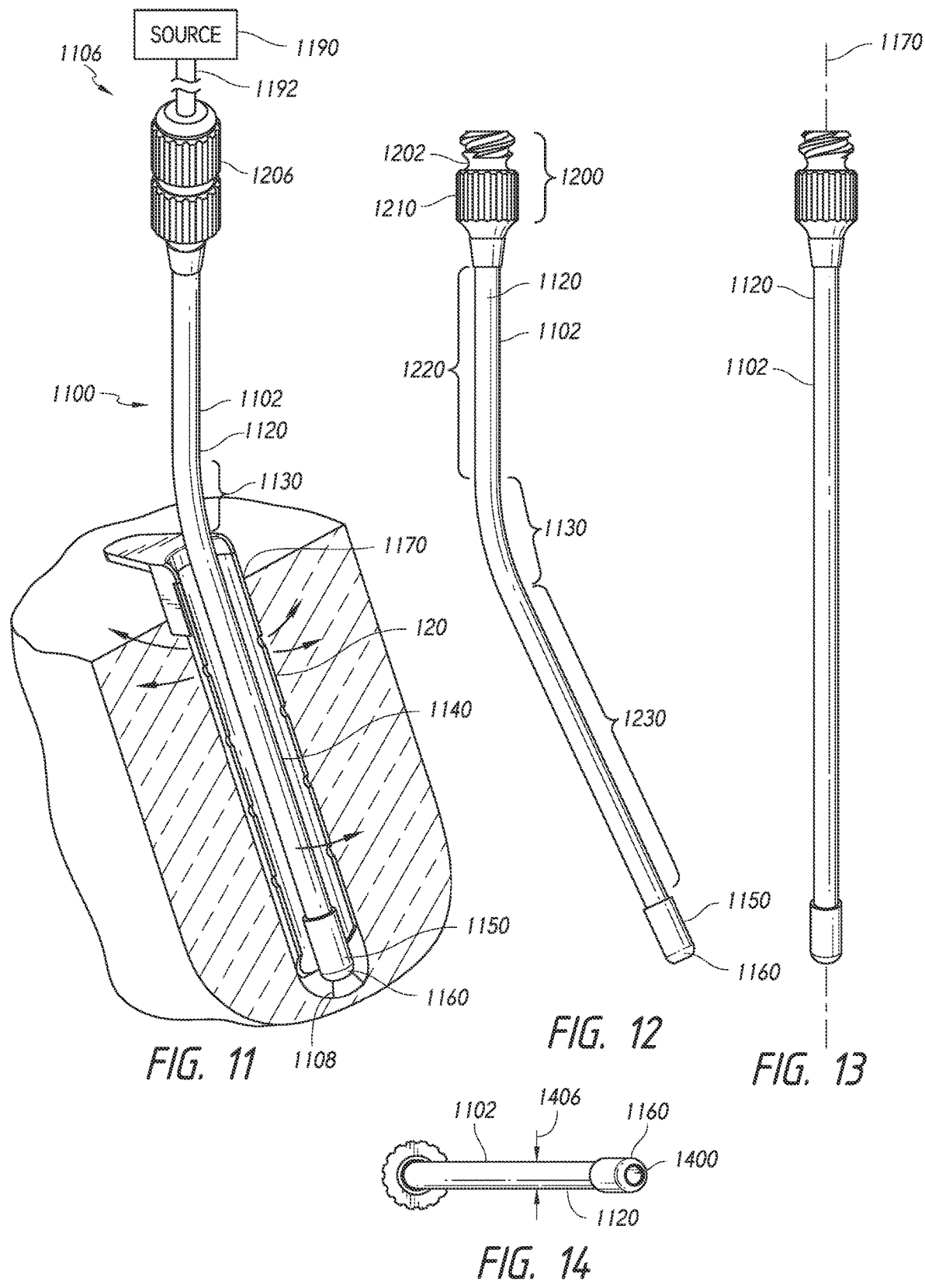

US 11,950,770 B1

MULTI-PORTAL SPLIT CANNULAS, ENDOSCOPIC HEMOSTATIC DISPENSERS AND SURGICAL TOOLS

TECHNICAL FIELD

The present disclosure relates generally to medical systems and, more particularly, to systems, devices, and methods for performing multi-portal surgical procedures.

BACKGROUND

Individuals often suffer from damaged or displaced spinal discs and/or vertebral bodies due to trauma, disease, degenerative defects, or wear over an extended period of time. One result of this displacement or damage to a spinal disc or vertebral body may be chronic back pain. A common procedure for treating damage or disease of the spinal disc or vertebral body may involve partial or complete removal of an intervertebral disc. An implant (commonly referred to as an interbody spacer) can be inserted into the cavity created where the intervertebral disc was removed to help maintain height of the spine and/or restore stability to the spine. An interbody spacer may also provide a lordotic correction to the curvature of the spine. An example of an interbody spacer that has been commonly used is a fixed dimension cage, which typically is packed with bone and/or bone growth-inducing materials. Unfortunately, it may be difficult to implant the interbody spacer at the intended implantation site between vertebral bodies. Additionally, conventional surgical techniques can cause a significant amount of trauma at or near the implantation site (e.g., injury to nerve tissue), which can significantly increase recovery time and lead to patient discomfort.

Spinal nerve compression can be caused by narrowing of the spinal canal associated with arthritis (e.g., osteoarthritis) of the spine, degeneration of spinal discs, and thickening of ligaments. Arthritis of the spine often leads to the formation of bone spurs, which can narrow the spinal canal and press on the spinal cord. In spinal disc degeneration, inner tissue of the disc can protrude through a weakened fibrous outer covering of the disc and can press on the spinal cord and/or spinal nerve roots. Ligaments located along the spine can thicken over time and press on the spinal cord and/or nerve roots. Unfortunately, spinal nerve compression can cause lower back pain, hip pain, and/or leg pain and may also result in numbness, depending on the location of the compressed nerve tissue. For example, spinal stenosis that causes spinal cord compression in the lower back can cause numbness of the legs. It is difficult to visualize internal tissue when removing tissue, often resulting in injury or removal of nerve tissue. Accordingly, there is a need for improved surgical systems, visualization techniques, and/or related technologies.

BRIEF DESCRIPTION OF THE DRAWINGS

FIG. 2A is a schematic top plan view showing surgical approaches to a lumbar spine for performing procedures.

FIG. 2B is an isometric view of the lumbar spine of FIG. 2A.

FIG. 11 illustrates an agent dispenser connected to a supply source and dispensing an agent in accordance with embodiment of the disclosure.

FIG. 12 is a side view of an agent dispenser in accordance with embodiment of the disclosure.

FIG. 13 is a top view of the dispenser of FIG. 12.

FIG. 14 is an end view of the dispenser of FIG. 12.

DETAILED DESCRIPTION

Figure 1:
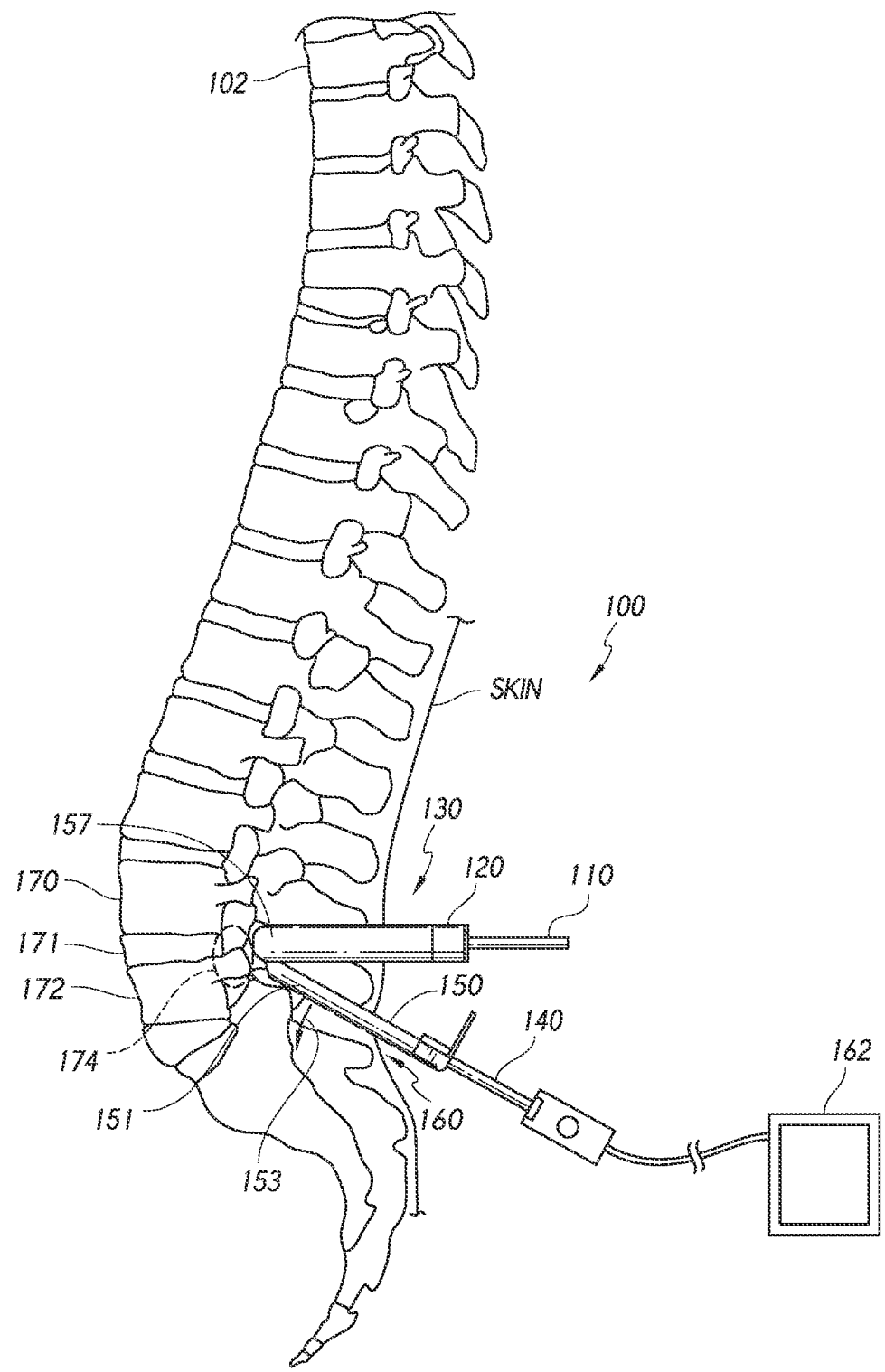
FIG. 1 is a side view of a multi-portal endoscopic surgical system in accordance with an embodiment of the disclosure.

The following disclosure describes various embodiments of medical systems, devices, and associated methods of use. At least some embodiments of a surgical system provide intraoperative visualization capability. A series of instruments can be delivered via portal sites and used to alter tissue (e.g., shape, crush, separate, cut, debulk, break, fracture, or remove tissue), create working spaces, create delivery paths, prepare an implantation site, implant a device, combinations thereof, or the like. Instrument and/or tissue visualization can help a physician identify issue, remove tissue under visualization, and/or prevent or limit injury or damage to non-targeted organs and tissues. In endoscopic-assisted surgeries, instruments and implantable devices can be precisely positioned using minimally invasive techniques to improve outcomes and reduce recovery times. Certain details are set forth in the following description and in the figures to provide a thorough understanding of such embodiments of the disclosure. Other details describing well-known structures and systems often associated with, for example, surgical procedures are not set forth in the following description to avoid unnecessarily obscuring the description of various embodiments of the disclosure.

A. Overview

At least some embodiments are directed to multi-portal surgical systems configured to treat patients with, for example, nerve compression, damaged or displaced spinal features (e.g., spinal discs, and/or vertebral bodies), or other conditions. For example, the surgical systems can be used to reduce or eliminate nerve compression, implant a fixed or expandable interbody device (e.g., devices to space apart vertebral bodies, restore stability of the spine, provide lordotic correction, etc.), perform discectomies, perform microdiscectomies, perform laminotomies, combinations thereof, or other surgical procedures. In decompression procedures, split cannulas can be used to access nerve compression sites. Visualization instruments can provide viewing of working spaces, tissue contributing to the nerve compression, and the tissue removal instruments. Tissue can be safely removed under endoscopic visualization.

Endoscopic techniques can be used to view, for example, the spine (e.g., vertebral spacing, vertebral alignment, etc.), tissue (e.g., damaged or displaced sections of intervertebral cartilage disc, tissue contributing to nerve compression, etc.), instruments and implants before, during, and after implantation, or the like. The visualization can help a physician throughout the surgical procedure to improve patient outcomes. In some embodiments, visualization instruments can be delivered through endoscopic cannulas (e.g., closed tubular cannulas, split cannulas, etc.). The cannulas can be held generally stationary or moved during one or more steps or the entire surgical procedure.

Access instruments can be selected based on the location of the working space. In some procedures, split cannulas of different lengths can be used to sequentially access and remove tissue. The sizes of the cannulas can be selected based on the location (e.g., depth) of the tissue, anatomical structures surrounding access paths and/or targeted tissue, and/or configuration of instrument(s). In some procedures, both tubular closed cannulas and split cannulas can be utilized. For example, a tubular closed cannula can prevent instruments from contacting tissue laterally adjacent to the cannula. The split cannula can allow the instrument to be moved laterally out of the cannula into a large working space in the patient. As such, instruments can be positioned in relatively large working spaces relative to an access port or incision in the skin (i.e., the incision can be significantly smaller than the size of the working space within the patient).

In some embodiments, multi-portal endoscopic techniques can be used to alter tissue at different locations along the spine. Bony features (e.g., facets and surrounding bone) of vertebrae can be removed to perform, for example, transforaminal procedures. The implantation site can be prepared by performing a discectomy, an interbody preparation procedure, or the like.

Multi-portal endoscopy-assisted methods can include performing at least a portion of a surgical procedure by using a first portal site. The first portal site can serve as a working portal for working instruments. At least a portion of the surgical procedure uses an endoscope positioned via a second portal site (e.g., a visualization portal) spaced apart from the first portal site. The spacing can be selected based on location and accessibility of the treatment site(s), whether along the spine or at another location. For example, the portals can be spaced apart to allow equipment (e.g., cannulas, endoscopes, working instruments, etc.) to be directed generally toward a working space within the subject.

In some decompression procedures, surgical steps can minimize or reduce pressure applied to nerve tissue and can include removing tissue contributing to stenosis, tissue pushing against nerve tissue, bulging sections of intervertebral cartilage disc, or the like. For example, tissue can be removed to enlarge an epidural space to reduce spinal cord compression.

In some aspects, techniques described herein relate to a multi-portal method for treating a subject. The methods include inserting a first distal end of a first split cannula into a first entrance formed in a subject. The first split cannula includes a first proximal end with a first flange configured to contact the subject's skin. A second distal end of a second split cannula can be inserted into a second entrance formed in the subject. The second entrance is spaced apart from the first entrance. The second split cannula includes a second proximal end with a second flange configured to contact the subject's skin. A distal end of an instrument positioned along a first passage of the first split cannula can be using a visualization instrument is positioned along a second passage of the second split cannula.

In some aspects, the technology relates to a split cannula including a port flange and a split shaft connected to the port flange. The split shaft includes a tapered distal end configured to penetrate tissue to position the port flange proximate to a subject's skin. The split shaft also includes a plurality of spaced apart motion inhibitors configured to contact tissue of a subject so as to inhibit movement of the split cannula relative to the subject.

In some aspects, the techniques described herein relate to performing a multi-portal spinal surgical procedure using first and second split cannulas. The multi-portal spinal surgical procedure can be a decompression procedure, an oblique lumbar interbody fusion procedure, a lateral lumbar interbody fusion procedure, a posterior lumbar interbody fusion procedure, a transforaminal lumbar interbody fusion procedure, an anterior lumbar interbody fusion procedure, or combinations thereof.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

B. Multi-Portal Surgical Systems

FIG. 1 is a side view of a spinal surgical system 100 ("system 100") positioned along a human subject's spine 102 in accordance with an embodiment of the disclosure. The system 100 can include an instrument assembly 130 and a visualization assembly 160. The instrument assembly 130 can include an instrument 110 and a split cannula 120. The visualization assembly 160 can include a visualization instrument 140 and a split cannula 150. The instruments 110, 140 can be moved distally and/or laterally out of the split cannulas 120,150, which can be positioned in incisions or endoscopic ports, to access a relatively large working space along the patient's spine. The split cannulas 120, 150 can have longitudinally-extending openings along their entire lengths or portion thereof (not visible in FIG. 1) to allow distal portions of the respective instruments 110, 140 to be moved laterally into and out of sides of the cannulas 120, 150.

The illustrated cannula 150 has an open front side 151 (illustrated facing the inferior direction relative to the patient) through which the instrument 140 can be moved, as indicated by arrow 153. The cannula 120 has an open front side (not visible in FIG. 1) facing the subject's spine such that a backside atraumatic surface 157 contacts tissue to limit, reduce, or substantially eliminate trauma to tissue. A series of instruments can be delivered through the split cannula 120. In some procedures, the instrument 110 can be used to remove tissue (e.g., intervertebral disc 171, tissue contributing to stenosis, etc.), form access paths to implantation sites, prepare an implantation site by, for example, moving organs or tissue (e.g., moving nerve tissue), prepare vertebral bodies (e.g., roughening or shaping vertebral endplates), or the like. The instrument 110 can be removed and a distraction instrument (e.g., one or more dilators) can be delivered through the cannula 120 to distract adjacent vertebrae 170, 172, thereby enlarging the intervertebral space. An interbody implant can be delivered through the split cannula 120, or another cannula (e.g., a non-split tubular cannula), and into the enlarged intervertebral space. In expandable implant embodiments, an expandable interbody fusion implant can be expanded to push apart vertebral endplates.

With continued reference to FIG. 1, the visualization assembly 160 can provide intraoperative endoscopic viewing of work spaces, delivery paths, organs, tissue (e.g., nerve tissue) implantation sites, implants, interbody fusion devices (e.g., before, during, and/or after delivery), instrument(s) (including dispensers, dilators, decompression instruments, etc.), and other areas or features of interest. The position of the cannulas 120, 150 can be selected based on the procedure and optical characteristics (e.g., field of view, zoom capability, etc.) of the visualization assembly 160. The visualization assembly 160 can moved throughout the procedure to provide intraoperative endoscopic viewing of one, multiple, or all of the surgical steps. For example, the visualization assembly 160 can be used to view tissue contributing to nerve compression caused by narrowing of the spinal canal associated with arthritis of the spine, degeneration of spinal discs, and thickening of ligaments. Arthritis of the spine often leads to the formation of bone spurs, which can narrow the spinal canal and press on the spinal cord. This tissue can be viewed using the visualization assembly 160. In spinal disc degeneration, the visualization assembly 160 can view the inner tissue of the disc protrudes through a weakened fibrous outer covering of the disc and pressing on the spinal cord and/or spinal nerve roots. The protruding tissue can be viewed before and/or during removal. The visualization assembly 160 can be used to also view ligaments pressing on the spinal cord and/or nerve roots to assist is treatment.

The visualization device 140 can be a low-profile fiber optic endoscope positioned directly through an incision, an endoscopic port, or the like. The visualization device 140 can include one or more endoscopes having, without limitation, fiber optics (e.g., optical fibers), lenses, imaging devices, working lumens, light source controls, or the like for direct viewing or viewing via a display 162 (e.g., an electronic screen, monitor, etc.). In some embodiments, the visualization device 140 can include a lumen through which fluid flows to irrigate the surgical site. For example, saline, or another suitable liquid, can be pumped through the visualization device 140 to remove tissue (e.g., loose tissue, bone dust, etc.) or other material impairing visualization. The visualization device 140 can also include one or more lumens (e.g., irrigation return lumens, vacuum lumens, etc.) through which the irrigation liquid can be withdrawn.

The visualization device 140 can illuminate the body cavity and enable high-resolution video visualization. A light source (e.g., a laser, light-emitting diode, etc.) located near or at the proximal end of the fiber optics can be used to transmit light to the distal end and provide illuminating light. This enables a surgeon to safely navigate into the subject's body and to illuminate specific body anatomy to view vertebral spacing, vertebral structures, nerves, bony buildup (e.g., buildup that could be irritating and pressing against nerves contributing to nerve compression), etc. In some embodiments, visualization optics for vision and illumination are included within the distal tip of the visualization device 140. The configuration and functionality of the visualization device 140 can be selected based on the desired field of view, viewing resolution, pan/zoom functionality, or the like. Irrigation techniques, visualization devices, instruments, cannulas, and visualization and surgical techniques are discussed in U.S. application Ser. No. 17/902,685 and U.S. application Ser. No. 16/687,520, which are incorporated by reference in their entireties.

FIG. 2A is a schematic top plan view along the lumbar spine of a human subject and illustrates example approaches for performing procedures suitable for the system 100 of FIG. 1 and other systems disclosed herein. FIG. 2B is an isometric view of the lumbar spine of FIG. 2A. Referring to FIGS. 2A and 2B, surgical equipment can be delivered via different paths, including an anterior lumbar interbody fusion (ALIF) path 210, an oblique lumbar interbody fusion (OLIF) path 220, a lateral or extreme lateral lumbar interbody fusion (LLIF or XLIF) path 230, a transforaminal lumbar interbody fusion (TLIF) path 240, and a posterior lumbar interbody fusion (PLIF) path 250. These paths can also be used to perform other procedures disclosed herein. For example, one or more of the paths 210, 220, 230 240, 250 can be selected for multi-portal endoscopic approaches to perform a wider array of lumbar spine procedures than conventional one-portal techniques. Cannulas can be positioned along the same path or different paths allow for independent positioning and manipulation of the endoscopic camera the surgical instruments, thereby providing greater flexibility and enhanced visualization of spinal anatomy.

Surgical instruments can remove tissue to define working space(s) inside the patient. In one example TLIF procedure, the transforaminal path 240 may be employed to implant a single small expandable or non-expandable interbody spacer at the intervertebral space. In one example PLIF procedure, two interbody spacers can be delivered along the posterior path 250 and implanted at the intervertebral space. The two interbody spacers can cooperate to keep the vertebral bodies at the desired spacing and may be larger than the TLIF spacer. Additionally, multiple interbody spacers can provide lordotic correction by providing support at different heights. In one example LLIF procedure, a single relatively large interbody spacer can be delivered along the lateral path 230 and implanted to provide asymmetrical support. In one example ALIF procedure, an asymmetric interbody spacer can be delivered along the anterior path 210 to provide support consistent with lordosis at that portion of the spine. Lateral approaches, transforaminal approaches, and anterior approaches can be used to access the cervical spine, thoracic spine, etc. The number of instruments, configurations of instruments, implants, and surgical techniques can be selected based on the condition to be treated.

FIGS. 3-5B show steps of example multi-portal surgical procedures performed on a human. Multi-portal techniques can be provided to access using a wide range of different trajectories. Advantageously, tissue can rest gently across openings of the split cannulas 120, 150 to help provide resistance when a user manually manipulates the instruments. The instruments can also be urged against the tissue to push the instruments out of the cannulas, thereby provide flexibility to access tissue in larger working spaces. Example surgical steps are discussed below.

Figure 3:
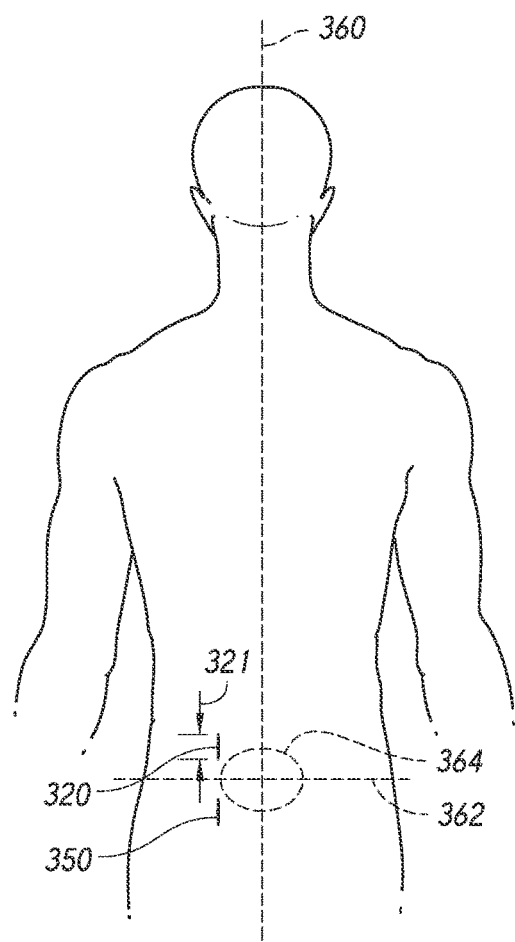
FIGS. 3-5B illustrate surgical steps for performing spinal procedures in accordance with embodiments of the disclosure.
Figure 4:
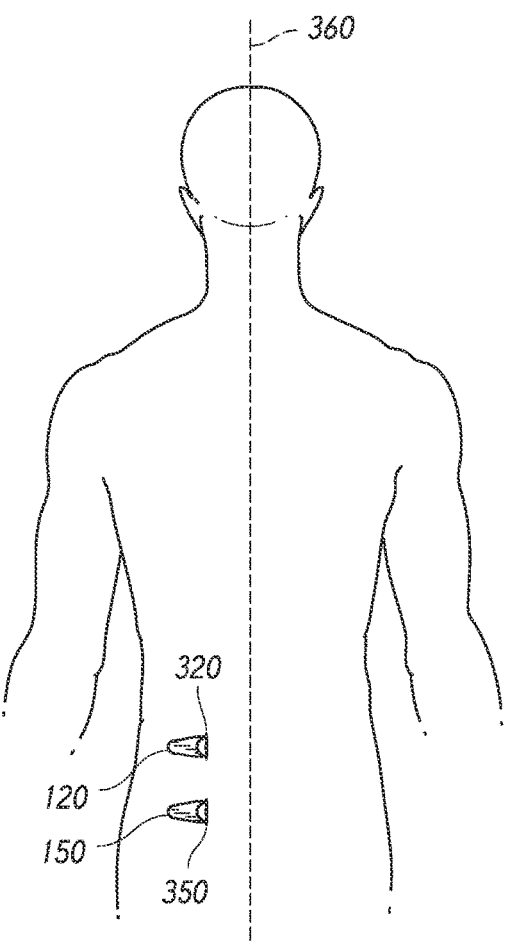

FIG. 3 shows two incisions 320, 350 for accessing the left side of a lumbar spine. FIG. 4 shows split cannulas 120, 150 positioned in the incisions 320, 350, respectively, for instrument insertion. The distance between the incisions 320, 350 can be equal to or less than the combined length of the cannulas such that distal ends of the cannulas can be moved adjacent to one another. In some embodiments, the distance between the incisions 320, 350 is equal to or less than an axial length of one, multiple, or all of the cannulas (e.g., cannulas 120, 150 in FIG. 4). The cannulas 120, 150 can be angled toward each other, as shown in FIG. 1, while maintaining a minimum distance of separation. Additional cannulas can be inserted into the subject to access other regions and/or provide alternative access paths.

Figure 5A:
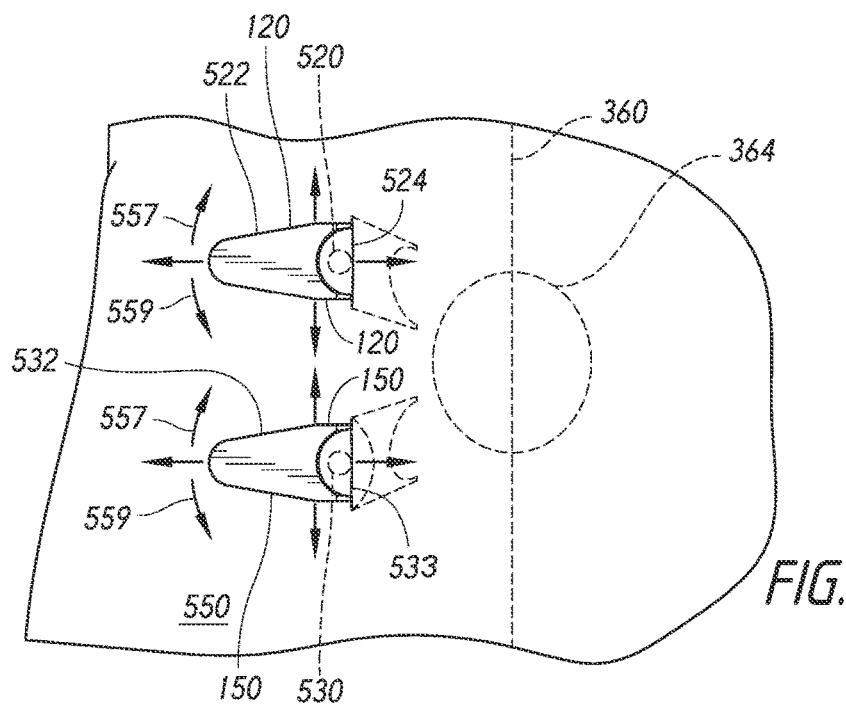

FIG. 5A shows instruments 520, 530 (illustrated in dashed line) positioned in U-shaped passages or channels of the cannulas 120, 150. The cannulas 120, 150 and instruments 520, 530 can be moved together or independently, as in indicated by arrows. Tissue 524, 533 extending across the open sides of the cannulas 120, 150 to help keep the retain portions of the instruments 520, 530 within the proximal ends of the cannula 120, 150. The cannulas 120, 150 can include insertion stops, illustrated as outwardly-extending flanges 522, 532, respectively, configured to contact the patient's skin 550. The cannulas 120, 150 and instruments 520, 530, respectively, can be positioned any number of times. Additionally or alternatively, additional incisions can be made along the patient to reposition the cannulas 120, 150 or insert additional cannulas and instruments.

Figure 5B:
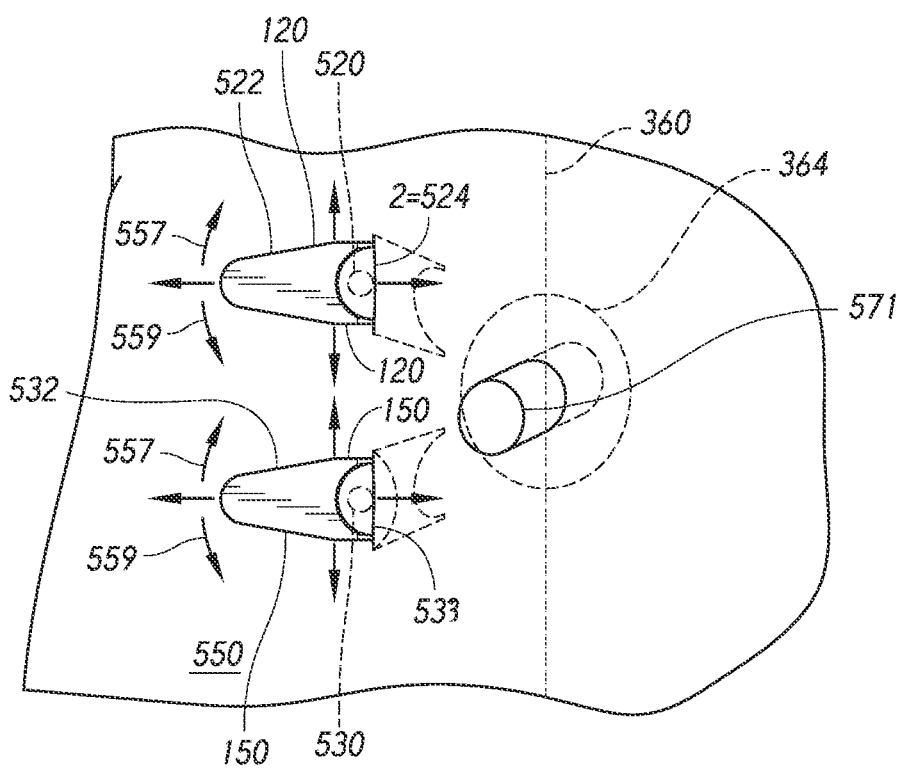

FIG. 5B shows a tubular cannula 571 positioned to deliver a spinal implant, such as an intervertebral cage, interspinous spacer, screws, etc. The tubular cannula 571 can also be positioned on the opposite side of the sagittal plane 360 or at other locations. Instruments, implants, and other items can be delivered through the tubular cannula 571.

The instruments 520, 530 of FIGS. 5A and 5B can be the same as or similar to the instruments of 110, 140 of FIG. 1 or other instruments disclosed herein, including instruments disclosed in U.S. application Ser. No. 17/902,685 and U.S. application Ser. No. 16/687,520. Details of surgical items are discussed in connection with FIGS. 6-15 and 20 and details of example surgical procedures are discussed in connection with FIGS. 16-19.

Figure 6:
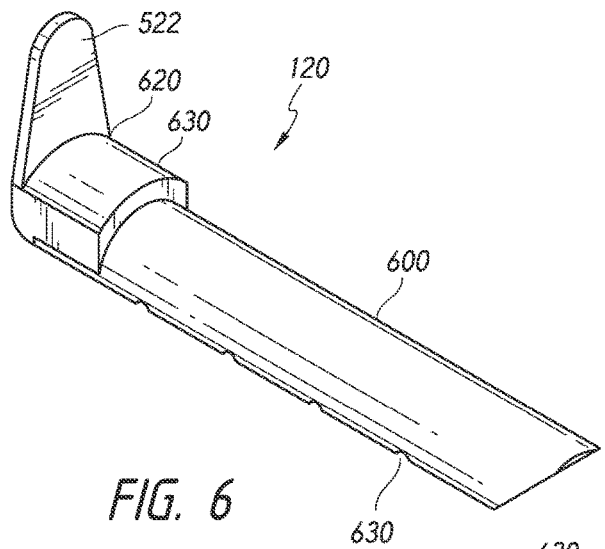
FIG. 6 is an isometric view of a split cannula in accordance with an embodiment of the disclosure.
Figure 7:
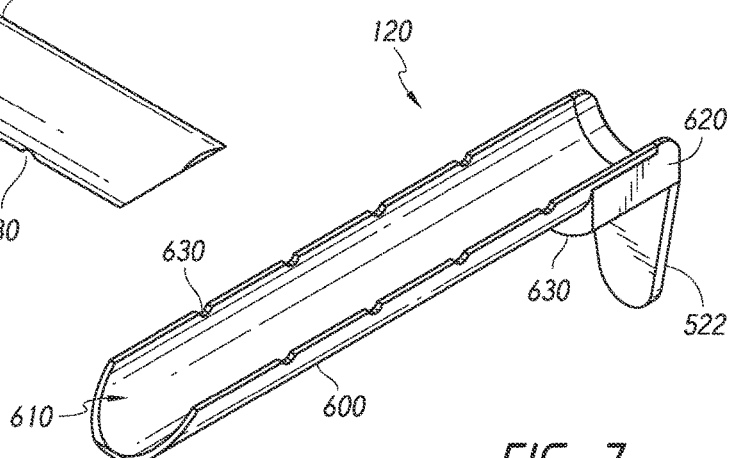
FIG. 7 is an isometric view of the split cannula of FIG. 6.

FIGS. 6-10 illustrate a split cannula 120 in accordance with an embodiment of the disclosure. Referring now to FIGS. 6 and 7, the cannula 120 can include an elongate split sleeve or shaft 600 ("split shaft 600"), a passage or channel 610 ("channel 610"), and a port flange 620. The split shaft 600 can include one or more motion inhibits 630 (one identified in FIG. 6 and another one identified in FIG. 7) configured to inhibit inadvertent axial movement when an instrument is moved relative to or withdrawn from the cannula 120. The port flange 620 can include the flange 522 and a thick-walled integral port body 630, which connects the flange 522 to the split shaft 600.

Figure 8:
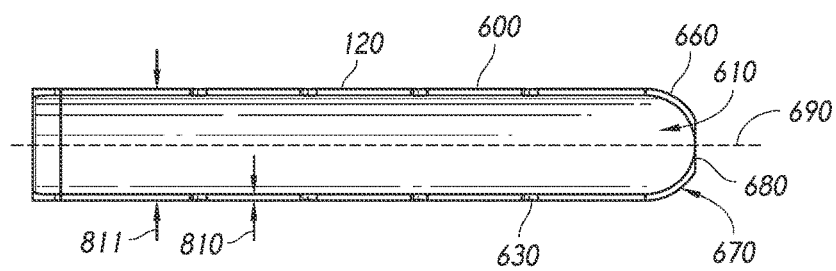
FIG. 8 is a frontal view of the split cannula of FIG. 6.
Figure 9:
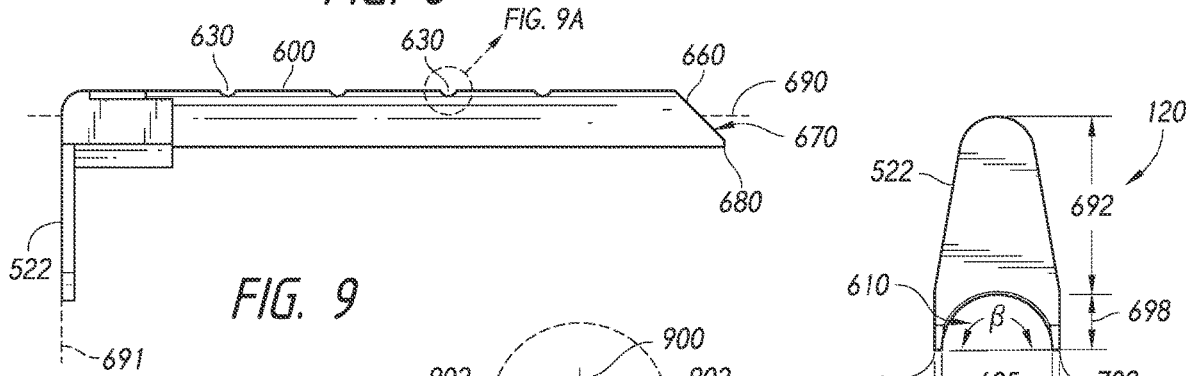
FIG. 9 is a side view of the split cannula of FIG. 6.

FIGS. 8 and 9 show a distal atraumatic distal portion 660 for piercing tissue. The distal portion 660 can include an angled surface 670 and a sharp tip 680. The angle (FIG. 9) of the surface 670 with respect to a longitudinal axis 690 can be selected based on desired penetrating capabilities. For example, the distal portion 660 configured to pierce adipose fat can be less sharp than the distal portion 660 configured to pierce muscle or tough connective tissue. The configuration of the distal portion 660 can be selected based on the characteristics of the tissue at the surgical site.

Referring now to FIG. 9, the flange 522 can extend radially outward from the longitudinal axis 690 of the cannula 120. In some embodiments, the flange 522 lies along an imaginary plane 691 that is generally orthogonal to the longitudinal axis 690. The configuration and orientation of the flange 522 can be selected based on the contours of the patient's skin, a trajectory from the incision to the working space, and other surgical parameters.

The motion inhibiters 630 can be evenly or unevenly spaced from one another and can be aligned or misaligned on opposite sides of the channel 610 (FIG. 8). The number, spacing, and dimensions (e.g., depth, width, etc.) of the motion inhibitors can be adjusted to reduce movement of the cannula during the procedure. This allows a user to focus on manually moving the instruments without holding the cannula. For example, a righted-handed user can hold the visualization instrument 140 of FIG. 1 in his/her left hand and manipulate the instrument 110 with his/her right hand. The cannulas can remain at the same general depth in the patient. The number and size of motion inhibitors can be increase to increase fixation or decreased to allow user to easily slide the cannula into and out of the patient. In some embodiments, for example, the motion inhibitors can be omitted to allow the cannulas to slide easily along tissue. The number, configuration, and spacing of the motion inhibitors can be selected based on the desired moveability of the cannula relative to adjacent tissue.

Figure 9A:
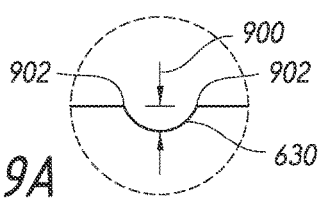
FIG. 9A is a detailed view of a motion inhibitor of FIG. 9

FIG. 9A is a detailed view of one of the motion inhibitors 630 in FIG. 9. The description of one motion inhibitor 630 applies to the other motion inhibitors 630 unless indicated otherwise. The motion inhibitor 630 can be a notch with a depth 900 greater than, equal to, or less than a wall thickness 810 (FIG. 8) of the split shaft 600. The motion inhibitor 630 can include corners or edges 902 configured to catch the patient's tissue, such as the patient's skin or shallow tissue, and can be V-shaped features, U-shaped features, or any other suitable shape features (e.g., indentations, grooves, cutouts, ridges, etc.). In some embodiments, the motion inhibitor 630 is a groove or protrusion extending circumferentially about the split shaft 600.

Figure 10:
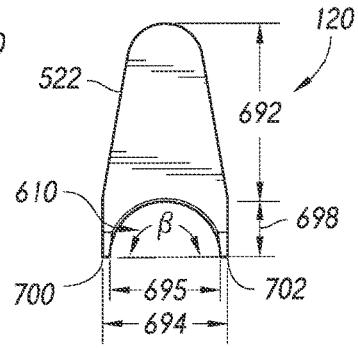
FIG. 10 is an end view of the split cannula of FIG. 6.

FIG. 10 is an end view of the cannula 120. The flange 522 has an axial length 692 longer than a maximum transverse or outer dimension 694 of the split shaft 600. In some embodiments, the axial length 692 can be longer than the outer dimension 694 (e.g., a distance between outer longitudinal edges 700, 702 of the shaft 600 or an outer diameter of the shaft 600), a width 695 of the channel 610, and/or a depth 698 at the channel 610. The width 695 can be, for example, 60 mm, 50 mm, 40 mm, 30 mm, 20 mm, or other dimensions selected based on the procedure to be performed. The flange 522 can prevent insertion of the entire cannula 120 into the patient. Because the maximum dimension of the flange 522 is greater than the maximum transverse dimension of the split shaft 600, the flange 522 can be longer than a length of an incision in which the shaft 600 is positioned.

With continued reference to FIG. 10, the curved channel 610 can define a sidewall with an arc length. In the illustrated embodiment, a central angle β is taken transversely along a plane generally orthogonal to the longitudinal axis 690 (FIG. 9) of the split shaft 600 and is about 180 degrees. In some embodiments, the central angle β is in a range of about 150 degrees and about 210 degrees, about 160 degrees to about 200 degrees, about 170 degrees to about 190 degrees, etc. The central angle β can be selected based on the procedure to be performed, instruments to be used, etc. Example transverse cross sections of channels are discussed in connection with FIGS. 10A-10D.

Figure 10A:
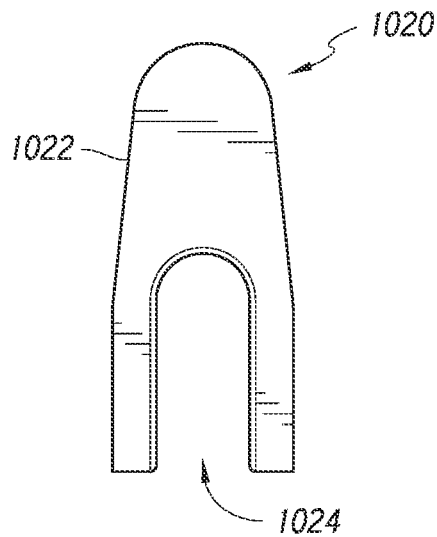
FIGS. 10A-10D are end views of split cannulas in accordance with embodiments of the disclosure.
Figure 10B:
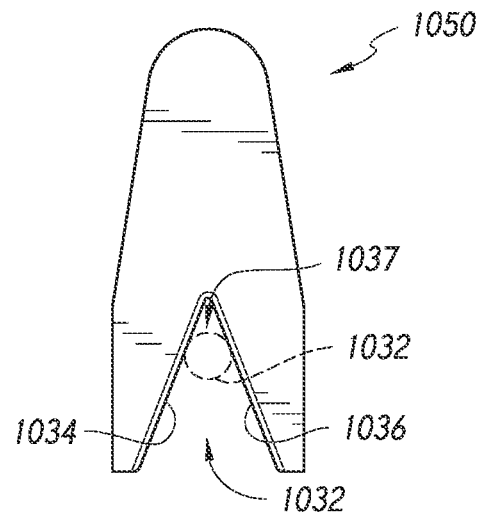

FIGS. 10A-10D are end views of cannulas in accordance with some embodiments. The description of the cannulas discussed in connection with FIGS. 1-10 applies equally to the cannulas of FIGS. 10A-10D except as indicated otherwise. FIG. 10A shows a cannula 1020 including an insertion stop 1022 and a U-shaped channel 1024, which is deeper than the partially circular channel 610 of FIGS. 6-10. FIG.

Figure 10C:
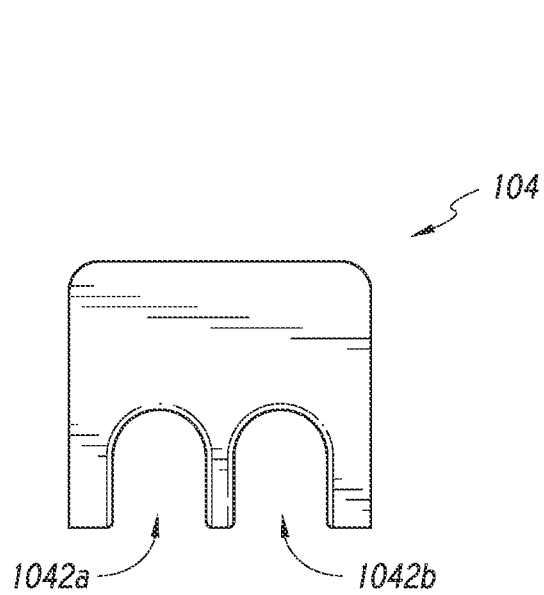
Figure 10D:
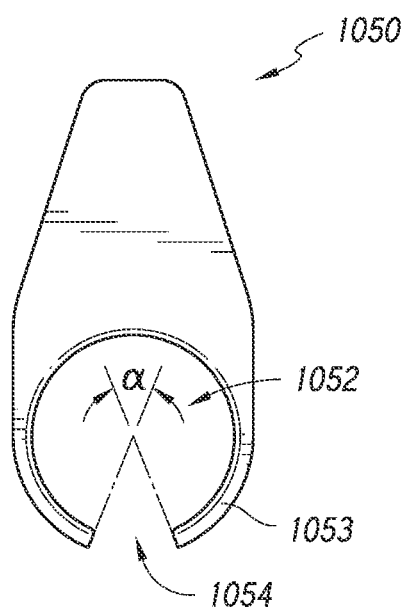

10B shows a cannula 1050 has a V-shaped cannel 1032 with generally flat sides 1034, 1036. An instrument 1032 (illustrated in phantom line) can be positioned at a bottom 1037 of the channel 1032. A user can use the channel bottom 1037 to help pivot the instrument 1038. FIG. 10C shows cannula 1040 including multiple channels 1042a, 1042b (collectively, "channels 1042") each configured to receive an instrument. Instruments can be simultaneously used in a side-by-side arrangement. The configuration, number, and positions of the channels 1042 can be selected based on the number and configuration of instruments to be simultaneously and sequentially utilized in a surgical procedure. FIG. 10D shows a cannula 1500 having a split shaft 1053 defining a channel 1052 that is wider than a channel opening 1054. The split shaft 1053 can define a central angle α between, for example, about 180 degrees and about 350 degrees, 200 degrees and about 330 degrees, 220 degrees and about 300 degrees, etc. This allows an instrument to be held captive in the channel 1052 during a wider range of movements. A sidewall of the split shaft 1053 can captive hold large instruments along the channel 1052 while allowing slender instruments to be moved through the opening 1054.

FIG. 11 shows a dispenser system 1100 dispensing a flowable substance 1108 into a patient. The dispenser system 1100 can include a dispenser wand 1102 ("dispenser 1102") and a supply system 1106. The supply system 1106 can include an agent source 1190, a line or conduit 1192, and connector 1206. The agent source 1190 can include, without limitation, one or more containers, vessels, pumps, controllers, and fluidic components (e.g., flow regulators, valves, etc.). Operation of pumps can be controlled based on characteristics of the agent. The flowable agent or substance 1108 ("agent 1108") can be a hemostatic agent configured to inhibit, prevent, or substantially eliminate bleeding alone or in conjunction with electrocautery or other surgical techniques, such as vessel ligation, suturing, etc. The hemostatic agent 1108 can include, without limitation, one or more sealing agents, glues (e.g., fibrin glues, gelatin-based glues, polyethylene glycol glues, etc.), glycol hydrogels, or the like. Additionally or alternatively, the agent 1108 can include one or more adhesives (e.g. tissue adhesives), medicants, imaging substances (e.g. radiopaque flowable gels, fluids, etc.), and other flowable substances. Multiple dispenser systems 1100 can be used in a procedure to dispense the same or different agents at the same or different locations. The dispenser 1102 can be moved laterally out of the stationary cannula 120. The configuration, length, and number of curved/straight sections of the dispenser 1102 can be selected based on the configuration of the cannula and steps to be performed. An example dispenser 1102 are described in connection with FIGS. 12-14.

FIGS. 12-14 show the dispenser 1102 in accordance with an embodiment of the disclosure. Referring now to FIG. 12, the dispenser 1102 can include a connector 1200, an elongated tubular body or wand 1120 ("wand 1120"), and an atraumatic tip 1150. The connector 1200 can be configured to connect to the supply system and can include a male coupling member 1202. In the illustrated embodiment, the coupling member 1202 is an externally threaded member couplable to a female connector 1206 of FIG. 11. The connector 1200 can also include a rotator 1210 with a knurled exterior, grooves, texturing, etc.

The wand 1120 can include a proximal straight portion 1220, an angled central portion 1130, and a distal straight portion 1230. The length of the proximal straight portion 1220 can be shorter than the length of the distal straight portion 1230. This allows the dispenser 1102 to extend through a cannula to access deep tissue while limiting the amount of the dispenser protruding from the patient. Advantageously, the relatively short proximal portion 1220 outside of the patient's body (shown in FIG. 11) limits the interference with working instruments. The angled portion 1130 is configured to align the distal straight portion 1230 with the cannula 120, as shown in FIG. 11.

FIG. 13 is a top view showing the wand 1120 lying generally along a plane 1170. FIG. 14 shows the tip 1150 configured for sliding or gliding along tissue while dispensing agent, thereby inhibiting, limiting, or substantially preventing trauma to internal tissue. The tip 1150 can have a curved smooth surface 1160 surrounding a dispensing opening 1400, which can have a diameter equal to or greater than least half the outer diameter 1406 of the wand 1120. This allows a relatively large volume of agent to be dispensed via the relatively narrow elongated body 1120.

In operation, if a physician identifies internal bleeding, the physician can deliver the dispenser 1102 through the cannula 120 of FIG. 11. The cannula 120 can be moved, indicated by arrows of FIG. 11, to direct the wand 1120 towards the target site. The dispenser 1102 can be delivered through the cannula 120 to position the atraumatic tip 1150 adjacent the site of bleeding. The supply system 1106 can deliver agent 1108 through the conduit 1192, through the dispenser 1102, and ultimately out the tip 1150. The dispensed agent 1108 can be a hemostatic agent that promotes hemostasis by initiating, promoting, or bypassing specific steps of the coagulation cascade.

C. Surgical Kits

Figure 15:
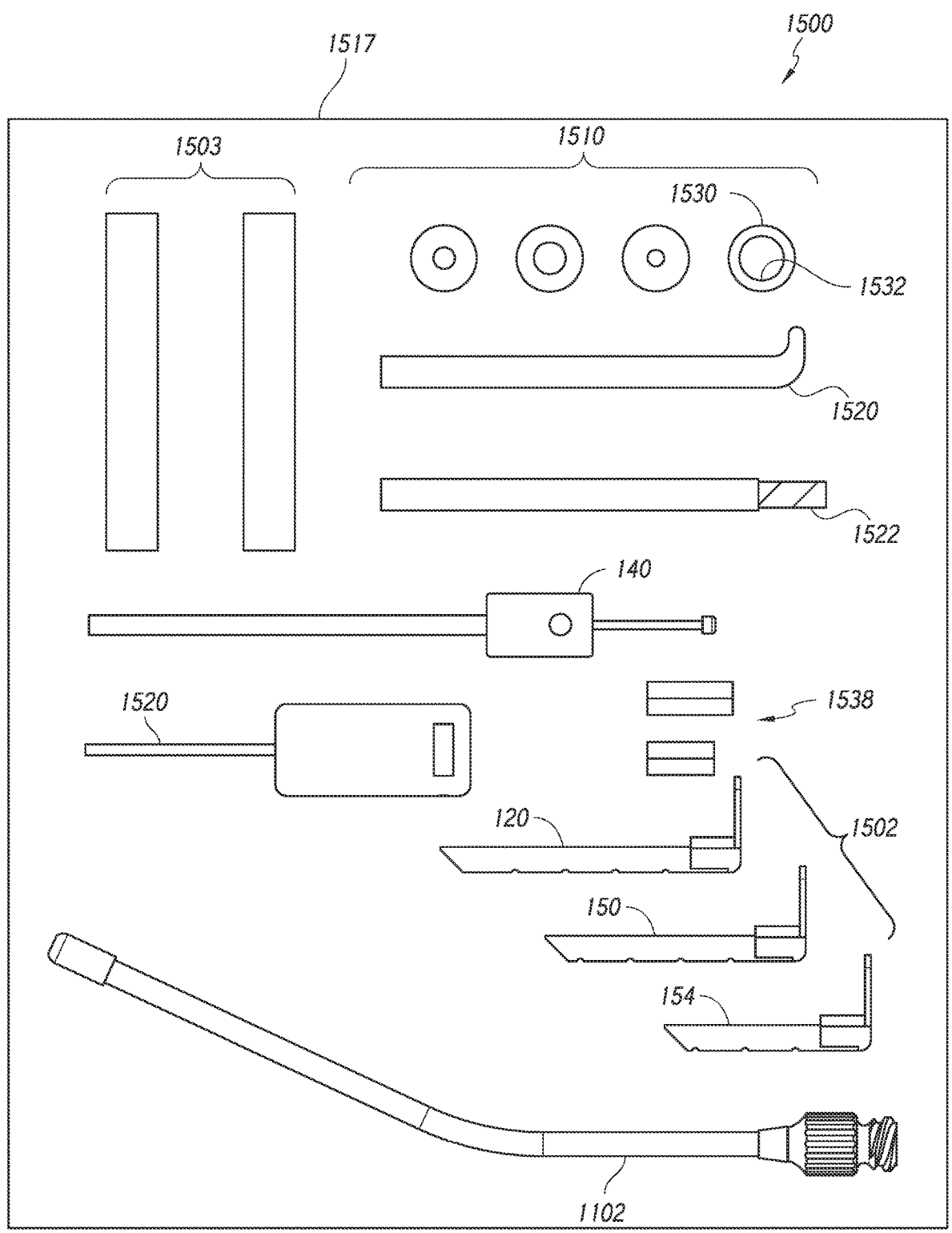
FIG. 15 is a plan view of a surgical kit in accordance with an embodiment of the disclosure.

FIG. 15 is a top plan view of a surgical kit 1500 that includes components discussed in connection with FIGS. 1-14. The kit can include a set 1502 of split cannulas, tubular closed cannulas 1503, a set 1510 of ports, agent dispenser 1102, and implants 1538. A physician can select appropriate cannulas based on the entrance sites. In the illustrative embodiment, the set 1502 includes three cannulas 120, 150, 154. A higher or lower number of cannulas can be provided and can be of the same or different sizes. For example, the cannulas 120, 150, 154 can have different lengths to provide flexibility to access internal sites. In some embodiments, portions of two or more of the cannulas 120, 140, 150 can be geometrically congruent. This allows for consistent usage of different instruments. For example, split shafts of cannulas can be geometrically congruent to provide for similar interaction instruments. The kit 1500 can include an optional connector (e.g., a rigid connector) to couple together cannulas (e.g., cannulas 120, 150, 154).

The kit 1500 can further include a plurality of decompression instruments. In the illustrated embodiment, the kit 1500 includes a debulking instrument 1520 and a reamer 1522. If the decompression instruments are utilized, a physician can select the port 1530 with a large opening. The kit 1500 can also include scalpels, dilators, rongeurs, or other surgical instruments. The kit 1500 can include components of, or the entire, visualization device 140, the distraction instrument 1510, the delivery or deployment instrument, and implantable devices 1538. The configuration and components of the kit can be selected based upon the procedure to be performed. Moreover, one or more of the kit's components can be disposable and can be made from metal, polymer, ceramic, composite, or other biocompatible and sterilizable material. The kit 1500 can include a container 1517 holding the components. The container 1517 can be a reusable or disposable box.

In operation, a user can select tools based on the location of the working space. In some procedures, split cannulas of different lengths can be used to sequentially access and remove tissue. The cannula configuration can be selected based on the location (e.g., depth) of the tissue, anatomical structures surrounding access paths and/or targeted tissue, and/or configuration of instrument(s). In some procedures, both tubular closed cannulas and split cannulas can be utilized. For example, a tubular closed cannula can prevent instruments from contacting tissue laterally adjacent to the cannula, as shown in FIG. 5B. The split cannula can allow the instrument to be moved laterally out of the cannula into a large working space in the patient. As such, instruments can be positioned in relatively large working spaces relative to an access port or incision in the skin (i.e., the incision can be significantly smaller than the size of the working space within the patient).

Systems, components, and instruments disclosed herein can be disposable or reusable. For example, components of the kit 1500 can be disposable to prevent cross-contamination. As used herein, the term "disposable" when applied to a system or component (or combination of components), such as a cannula, port, dispenser, instrument, tool, or a distal tip or a head (e.g., a reamer head, rongeur, etc.), is a broad term and generally means, without limitation, that the system or component in question is used a finite number of times and is then discarded. Some disposable components are used only once and are then discarded. In other embodiments, the components and instruments are non-disposable and can be used any number of times. The cannulas 120, 150, 154, dispenser 1102, and other kit components can be reusable or disposable and configured to be used with one another.

D. Surgical Techniques

Figure 16:
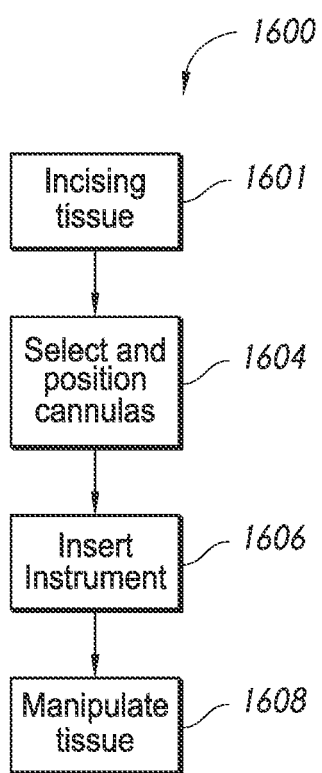
FIG. 16 is a flow diagram illustrating a method for performing a spine surgery in accordance with an embodiment of the disclosure.

FIG. 16 is a flow diagram illustrating a method 1600 for performing a spine surgery in accordance with an embodiment of the disclosure. In block 1601, incisions can be made in the subject's tissue to create portal sites (e.g., entrances). Referring now to FIG. 3, first and second entrances 320, 350 can be positioned on the same side of the subject's midsagittal plane 360 and can be formed by generally linear sagittal incisions aligned with and generally equidistant (e.g., distances ±5%, ±3%, etc.) from the midsagittal plane 360. The first and second entrances 320, 350 can be positioned on either side of a transverse plane 362 passing through a target site 364. In other embodiments, the first and second entrances 320, 350 can be positioned on opposite sides of the subject's midsagittal plane 360. In yet other embodiments, the first and second entrances 320, 350 can be located along the subject's midsagittal plane for midline approaches or procedures.

In block 1604 of FIG. 16, cannulas can be selected and then positioned in the patient. Preoperative imaging can be used to view anatomical structures. Cannulas can then be selected from a kit (e.g., kit 1500 of FIG. 15) based on the imaging. Fluoroscopy can be used to view radiopaque items (e.g., radiopaque disposable or reusable cannulas 120, 150, 152) being inserted into and/or repositioned in the patient, thereby avoiding injury or trauma to non-targeted tissue. Intraoperative imaging can also be used during any or all of the other steps of method 600 to view, for example, all or portions of the cannulas, working spaces, and/or surgical sites.

In block 1606, instruments are inserted through the cannulas. Imaging can be used to monitor the insertion and positioning of the instruments. The imaging can be external imaging (e.g., real-time fluoroscopy viewable by the surgical team) and/or endoscopic imaging. The instruments can be inserted manually, robotically, or other suitable technique.

In block 1608, instruments are used to manipulate tissue. The subject's shallow tissue can help hold instruments in passageways in the split-cannulas while the deeper tissue is removed. Fluoroscopy, MR imaging, CT imaging, direct visualization, or other visualization techniques can be used in addition to or in lieu of the endoscopic viewing. Additional instruments can be sequentially delivered through the cannulas. In some procedures, multi-modality imaging of the target site can be performed using an external imaging device (e.g., X-ray machine, fluoroscopy system, etc.) and a visual visualization instrument. Intraoperative imaging can be displayed via a digital screen in the surgical room. Example procedures for manipulating tissue using the method 1600 of FIG. 16 are discussed in connection with FIGS. 17A-18B.

Figure 17A:
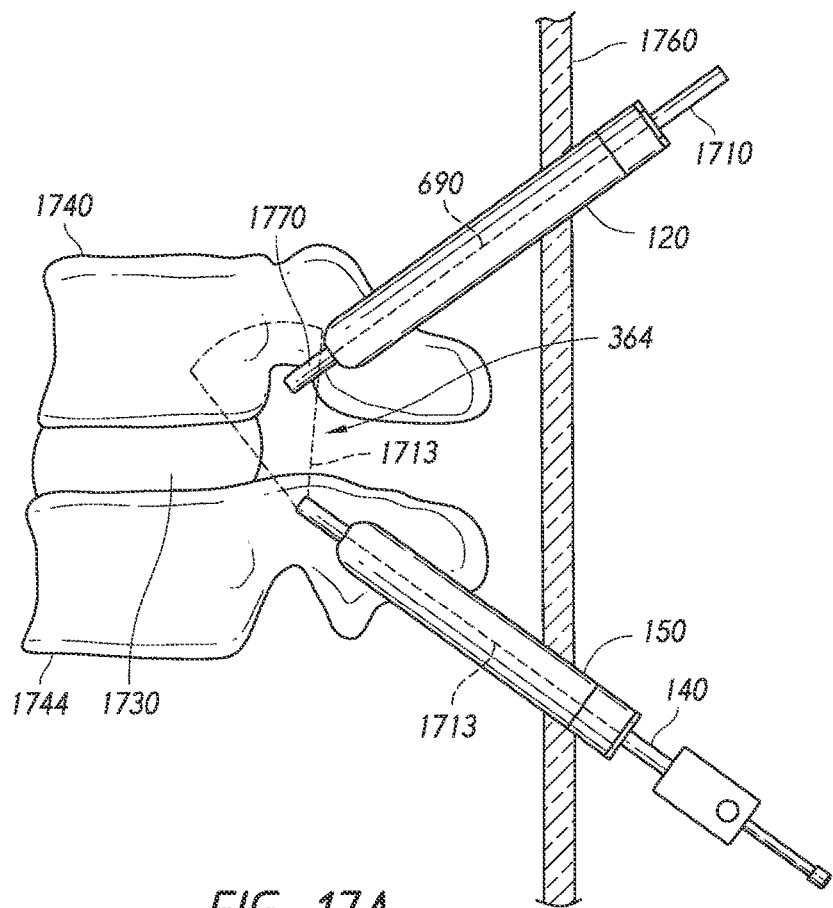
FIGS. 17A-17B are side views of multi-portal surgical systems at different positions in accordance with an embodiment of the disclosure.
Figure 17B:
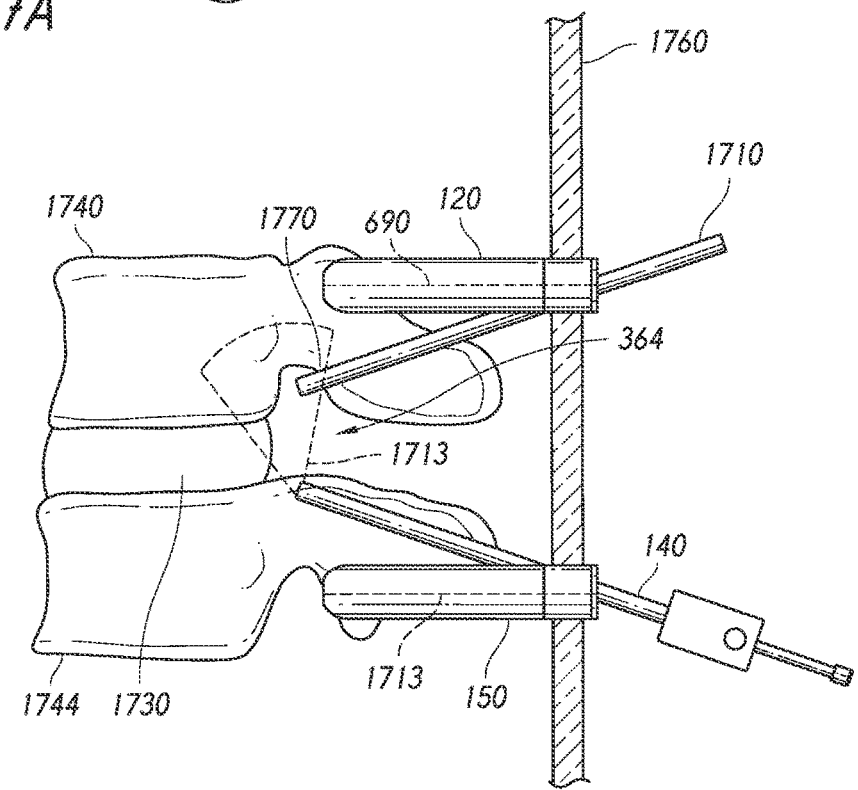

FIGS. 17A-17B are side views of multi-portal surgical systems at different positions in accordance with an embodiment of the disclosure. The cannulas 120, 150 extend through the subject's skin 1760 (thickness not illustrated at scale) at different locations and orientations. The visualization instrument 140 has a field of view 1713 suitable for viewing the spinal column and can be positioned using, for example, a transforaminal approach, a posterior approach, or a lateral approach. To allow significant instrument movement, the cannulas 120, 150 can have axial lengths shorter than a distance from the incision in the skin 1760 to the spine. The sizes of the cannulas 120, 150 can be selected based on the size and configuration of the incision and characteristics of the tissue. For example, the enlarged port body of the cannula can be sufficiently long to extend through the subject's skin, fascia, and muscle. The channel of the cannulas can be sufficiently large to allow instruments to be inserted into and distally along the channel, which can prevent or inhibit tearing of tissue. The tissue can cover the channel to keep at least the proximal position of the instrument in the cannula. Instruments can have relatively small diameters relative to a width of sidewall openings of the cannulas to limit or inhibit tearing of the tissue around the incision. In some procedures, ports can be installed in some incisions and cannulas can be installed in other incisions without ports. A physician can determine whether to install ports based on the instruments to be utilized and the position of the incisions. Cannulas, ports, and other components can be installed in each of the incisions. Details of example procedures are discussed in connection with FIGS. 17A-18B.

Referring to FIGS. 17A and 17B together, the visualization instrument 140, which is outside intervertebral spaces, is positioned to view at least a portion of an intervertebral disc 1730, vertebral bodies 1740, 1744, and/or the distal portion 1770 of the instrument 1710. Fluoroscopy, MR imaging, CT imaging, direct visualization, or other visualization techniques can be used in addition to or in lieu of the endoscopic viewing. Additional instruments can be sequentially delivered through the cannula 120. In some procedures, multi-modality imaging of the target site can be performed using an external imaging device and the visual visualization instrument 140. The intra-operative imaging can be displayed via one or more digital screens (e.g., endoscopic imaging and fluoroscopy on different screens) in the surgical room.

FIG. 17A shows the cannulas 120, 150 angled toward a vertebral level to allow instruments 140, 1710 to be kept generally aligned with the respective cannulas 150, 120.

FIG. 17B shows the cannulas 120, 150 kept generally perpendicular to the subject's spine and the instruments 1710, 140 are angled toward a vertebral level. The cannulas 120, 150 can be manually moved between the positions of FIGS. 17A and 17B. In other procedures, cannulas 120, 150 can be kept at the same general position during one or more steps of the procedure.

Figure 18A:
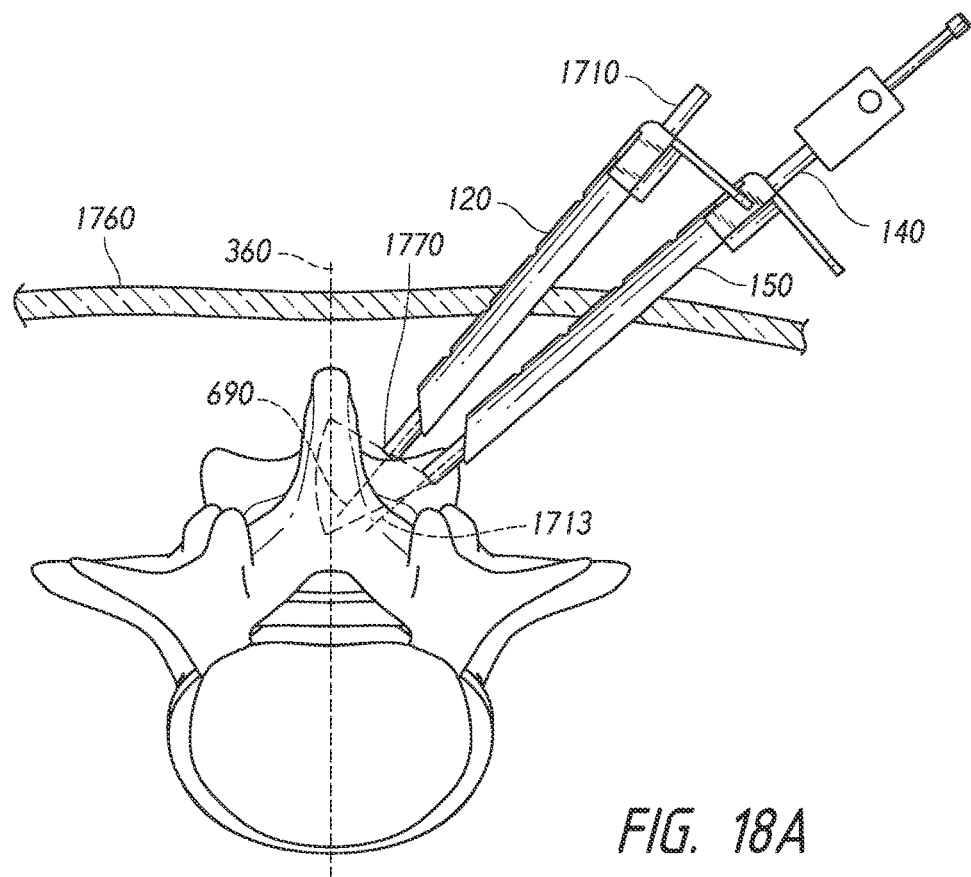
FIGS. 18A-18B are superior-to-inferior views of the multi-portal surgical system at different positions in accordance with an embodiment of the disclosure.
Figure 18B:
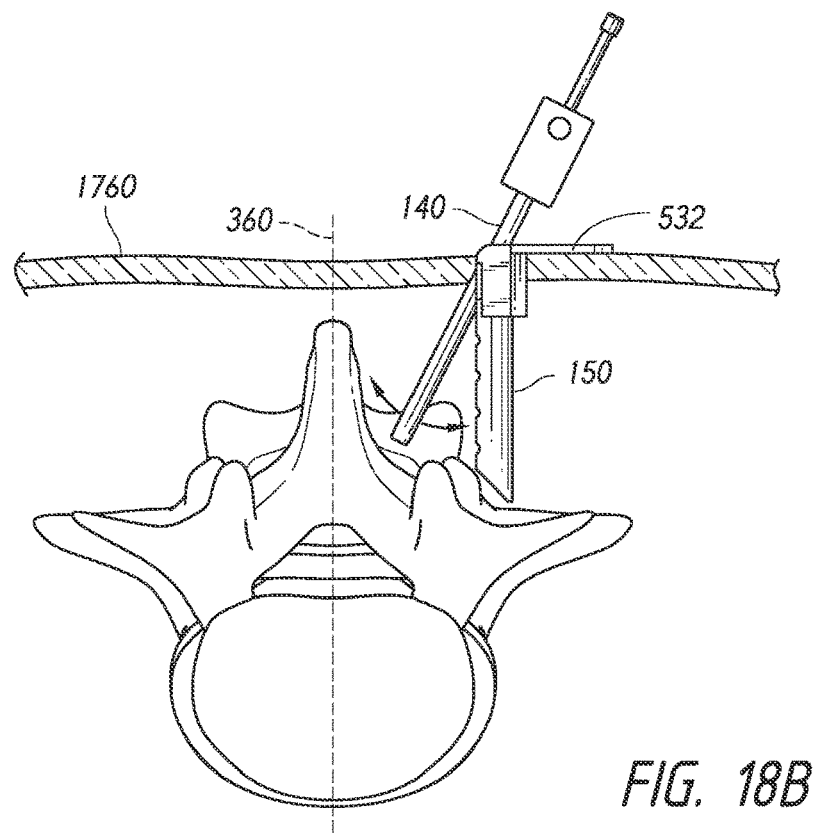

FIGS. 18A-18B are superior-to-inferior views of the multi-portal surgical system at different positions in accordance with an embodiment of the disclosure. Open sides of one or both cannulas 120, 150 can face the subject's midsagittal plane 360. The distal ends of the cannulas 120, 150 can be moved relative to the spine while the proximal ends of the cannulas 120, 150 remain generally stationary (e.g., at a fixed axial position relative to the skin 1760). Distal portions of the instruments 520, 530 can extend out of longitudinally-extending openings of the cannulas 120, 150 to manipulate the tissue at the target site while shallow tissue (e.g., skin 1760) retains the respective cannulas 120, 150.

Referring now to FIG. 18A, longitudinal axes 690, 1713 of the cannulas 120, 150, respectively, are generally directed toward a vertebral level along the subject's spin, targeted tissue, or the like. Example cannula 150 of FIG. 18B is shorter than the cannula 150 of FIG. 18A and oriented to be generally parallel to the midsagittal plane 360. FIGS. 17B and 18B show flanges of shorter cannulas 120, 150 adjacent to or against the surface of the skin 1760. The lengths of the cannulas can be selected based on external imaging of the surgical site, access path, and adjacent anatomical features.

The length of the incisions can be selected to help inhibit limit axial rotation of the cannulas. A ratio of the length of the incision to an outer width of the cannula can be less than or equal to, for example, 1.1, 1.2, 1.3, 1.4, or 1.5. For example, a ratio of a length 321 of the incision 320 of FIG. 3 to a transverse width split shaft width 811 of FIG. 8 can be equal to or less than 1.5 to inhibit or prevent 90 degrees (e.g., half of the arc of the channel 610 of FIG. 10) of rotation of the cannula 120 about its longitudinal axis 690 (FIGS. 8 and 9). This keeps the open side of the cannula 120 generally facing the working space (e.g., working space along the subject's spine in FIGS. 18A and 18B). Referring again to FIGS. 5A and 5B, the cannulas 120, 150 can be rotate (indicted by arrows 557, 559) less than 70 degree, 80 degrees, or 90 degrees without tearing the patient's surrounding skin. The patient's skin can inhibit larger rotations to prevent the likelihood improper positioning of instruments. The configurations equipment and locations and configurations of incisions can be selected based on the anatomy and procedure.

Instruments can be selected to treat, without limitation, spinal nerve compression (e.g., spinal cord compression, spinal nerve root compression, or the like), spinal disc herniation, osteoporosis, stenosis, or other diseases or conditions. Referring now to FIGS. 17A-18A, after access the work space, the tissue removal tip 1770 can remove unwanted tissue, including, without limitation, tissue bulging from discs (e.g., disc 1730 of FIGS. 17A and 17B), bone (e.g., lamina, lateral recesses, facets including the inferior facets, etc.), bone spurs (e.g., bone spurs associated with osteoarthritis), tissue of thickened ligaments, spinal tumors, displaced tissue (e.g., tissue displaced by a spinal injury), or tissue that may cause or contribute to spinal nerve compression. The instrument 1710, as well as other instruments (e.g., rongeurs, debulkers, scrapers, reamers, dilators, etc.), can be used to perform one or more dilation procedures, decompression procedures, discectomies, microdiscectomies, laminotomies, or combinations thereof. In procedures for treating stenosis, the instrument 1710 can be used to remove tissue associated with central canal stenosis, lateral recess stenosis, and/or other types of stenosis. In some decompression procedures, the instrument 1710 can be a tissue removal device used to, for example, remove bone, separate the ligamentum flavum from one or both vertebrae 1740, 1744 (FIGS. 17A and 17B), cut or debulk the ligamentum flavum, remove loose tissue, and remove at least a portion of the intervertebral disc. Each stage can be performed with a different instrument.

The visualization device 140 of FIGS. 17A and 17B can be, without limitation, an endoscopic instrument that includes fiber optics suitable to image the treatment site and surrounding tissues, such as the spinal cord, nerves branching from spinal cord, ligament, vertebrae 1740, 1744, intervertebral disc 1730, or any other features or anatomical structures of interest while the instrument 110 removes tissue (e.g., bone from the vertebrae 1740, 1744, intervertebral disc 1730, etc.). Surrounding non-targeted tissue can be viewed to ensure that the instrument 1770 does not injure it. This allows a physician to remove tissue without damaging nerve tissue, the spinal cord, and other non-targeted tissue. The instrument 140 can have irrigation channels to circulate fluid through the working space to help remove blood, lose tissue, and other anatomical features that may obscure viewing.

Referring to FIGS. 17A-18B, the visualization device 140 can be a steerable to facilitate navigation around anatomical features. The visualization device 140 can include a fiberoptic scope, or a flexible or rigid instrument with one or more illumination elements (e.g., fiber optics for illumination) or imaging elements (e.g., charge-coupled devices for imaging) suitable for visualizing the interior of otherwise inaccessible sites. In some embodiments, the visualization device can be rod-lens endoscopes with an outer diameter equal to or smaller than about 2 mm, 3 mm, 4 mm, 5 mm, 6 mm, 8 mm, or 10 mm; and a length equal to or shorter than about 15 cm, 20 cm, 30 cm, or 40 cm. The visualization device 140 can also an integrated irrigation features (e.g., valves, flow control buttons, fluid lumens, return lumens,), connectors (e.g., electrical connectors, fluidic connectors, etc.), access ports (e.g., access ports connected to lumens (e.g., lumens through which instruments can pass)), or the like. In embodiments with an angled lens, the visualization instrument can have approximately 0 degree, 10 degree, 15 degree, 30 degree, or 45 degree lens angles, which are toward a light source. In other angled lens embodiments, the visualization instrument can have an approximately 15 degree, 30 degree, or 45 degree lens angled away from a light source. The angle of the lens can be selected based on the area to be viewed. In some posterior or lateral spinal procedures, a 0 degree lens can provide a wide-angle view suitable for viewing nerve roots, the spinal cord, and intervertebral space. A 30 or 45 degree lens endoscope angled toward the light source can be used to provide an angled view toward, for example, the spine or midsagittal plane to view, for example, the spinous processes, spinal cord, central regions of the intervertebral space. A 30 or 45 degree lens endoscope angled away from the light source can be used to provide an angled view toward the lateral features or the spine, such as nerve roots at the neural foramen, side regions of the intervertebral space, or the like.

Figure 19:
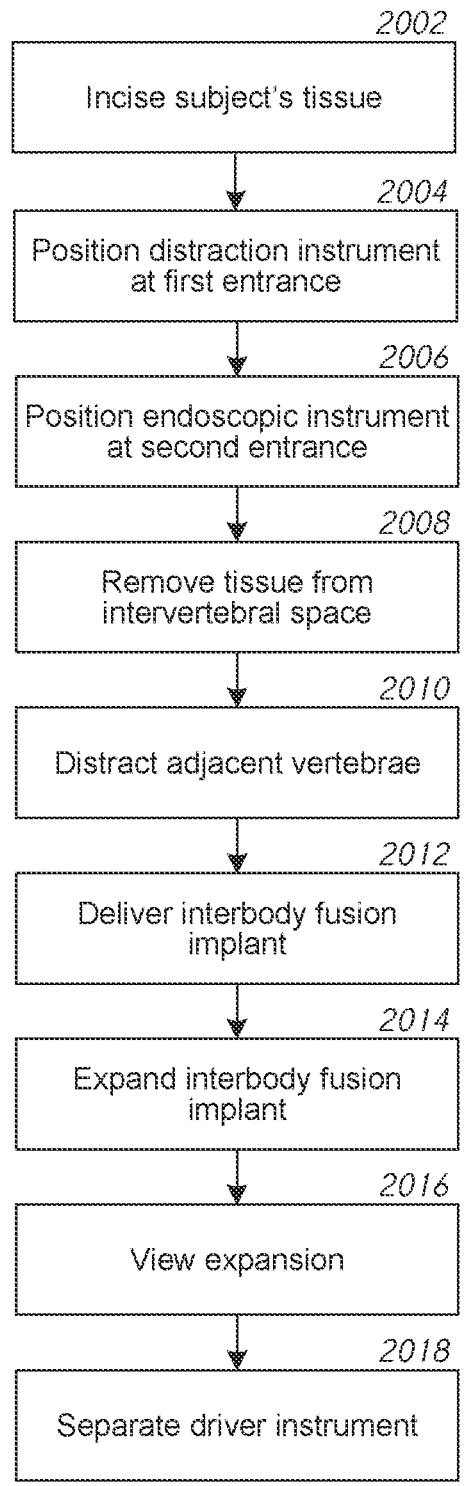
FIG. 19 is a flow diagram illustrating treatment methods in accordance with embodiments of the disclosure.

FIG. 19 is a flow diagram illustrating a surgical method for implanting an implant in accordance with an embodiment of the disclosure. The surgical steps of FIG. 19 can be incorporated into other surgical methods (e.g., methods of FIGS. 3-5B and method 1600 of FIG. 16) disclosed herein.

In block 2002, incisions can be made in the subject's tissue to create first and second portal sites (i.e., entrances). In some embodiments, the first and second entrances can be positioned on the same side of the subject's midsagittal plane. In other embodiments, the first and second entrances can be positioned on opposite sides of the subject's midsagittal plane. In yet other embodiments, the incisions can be made along the subject's midsagittal plane.

Optional ports can be installed in each of the entrances. The sizes of the ports can be selected based on the size of the incision and characteristics of the tissue at the port site. For example, a tubular body of the port can be sufficiently long to extend through the subject's skin, fascia, and muscle. An access opening of the port can be sufficiently large to allow instruments to be inserted into and through the ports, which can prevent or inhibit tearing of tissue. Instruments can be delivered through the incisions into the patient without utilizing ports. Such instruments can have relatively small diameters to limit or inhibit tearing of the tissue around the incision. In some procedures, ports can be installed in some incisions and instruments can be installed in other incisions without ports. A physician can determine whether to install ports based on the instruments to be utilized and the position of the incisions.

In block 2004, a distraction instrument can be positioned at the first portal site by inserting the distraction instrument through, for example, an installed port. In some procedures, a cannula can be positioned in the port and the distraction instrument can be delivered through the lumen of the cannula. In other embodiments, the distraction instrument can be inserted directly into the port without utilizing the cannula.

In block 2006, a visualization device can be positioned at a second portal site by delivering the visualization device through a port. The visualization device can be installed with or without use of the cannula. In some embodiments, the visualization device can be a low-profile fiber optic visualization system deliverable through a portal site in the form of a small incision. In these procedures, a cannula may not be used since the visualization device has a small diameter. The visualization device can be kept at the same portal site throughout most of the surgical procedure period in which the spine is altered. For example, the visualization device can be positioned at a single portal site for at least 80% or 90% of the surgical period in which instruments are positioned in the subject. The visualization device can be positioned within the subject such that an interbody fusion device is capable of being implanted without removing the endoscope from the subject. This can reduce the overall surgery time.

A steerable visualization device can be used to facilitate navigation around anatomical features. The steerable visualization device can include a fiberoptic scope, or a flexible or rigid instrument with one or more illumination elements (e.g., fiber optics for illumination) or imaging elements (e.g., charge-coupled devices for imaging) suitable for visualizing the interior of otherwise inaccessible sites. In some procedures, multiple visualization instruments are utilized. In one procedure, multiple visualization instruments are positioned within the same port, which is large enough to allow relative movement between the endoscopic instruments. In other procedures, endoscopic instruments are positioned in spaced apart ports. To provide bilateral viewing, a first port and first endoscopic instrument can be positioned on one side of the midsagittal plane of the subject, and the other port and endoscopic instrument can be positioned on the other side of the midsagittal plane. Multiple visualization instruments used in a single procedure can have different viewing characteristics.

The images of the subject's spine can be used to determine implantation information about the interbody fusion implant. Implantation information can include, without limitation, a recommended interbody fusion implant, expansion setting for the interbody fusion implant, and/or recommended implantation position for the interbody fusion implant. The user can be presented information for viewing based on the analysis of the image data, including information for repositioning the interbody fusion implant or information for collapsing the interbody fusion implant.

In block 2008, tissue from the intervertebral space can be removed with a tissue removal device positioned at the first entrance. In block 2010, adjacent vertebrae can be distracted using the distraction instrument to enlarge the intervertebral space between the adjacent vertebrae. In block 1012, an interbody spacer, such as an interbody fusion implant, can be delivered to the enlarged intervertebral space. The interbody fusion implant can be delivered in a collapsed configuration through a lumen of the distraction instrument. In block 2014, the interbody fusion implant can be expanded laterally and vertically while a driver instrument is positioned within the distraction instrument positioned at the first entrance and while being endoscopically viewed in block 2016. The lateral and vertical expansion of the interbody fusion implant can be sequential. For example, after the interbody fusion implant is horizontally expanded, the interbody fusion implant can be vertically expanded to provide disc height restoration.

In block 2016, image data can be obtained by an endoscopic instrument. The image data can be video, still images, or other image data. Image data can be obtained before, during, and/or after expansion and analyzed with endoscopic visualization to confirm the position of the expanded interbody fusion implant to improve efficacy of surgeries by allowing the physician to visually assess the procedure. For example, a first image of an implantation site can be obtained by the endoscopic instrument. A second image of the implantation site can be obtained using the endoscopic instrument after delivery of the interbody fusion implant. Image data can be analyzed to determine whether the expanded interbody fusion implant is located at a deployment position based on a position of the expanded interbody fusion implant shown in the second image.

In some embodiments, the first image and the second image can be compared to determine the position of the expanded interbody fusion implant. If the interbody fusion implant is mispositioned, the user can be notified of the mispositioning. The notification can be via an audible alert, visual alert (e.g., an alert displayed on the display 162 at FIG. 1), or by other suitable notification means. In block 2018, the driver instrument can be separated from a locked expanded interbody fusion implant. The implanted interbody fusion implant can be visualized to confirm proper positioning and deployment of the implant. Visualization can be used if additional procedures are performed. Additional procedures may include, without limitation, delivering bone, growth-promoting materials, or the like to the intervertebral space. Visualization can also be used to view other procedures, such as fixation procedures involving pedicle screws, interspinous spacers, or the like.

The method of FIG. 19 can be performed using various systems disclosed herein. Additional instruments and steps can be performed as needed to provide treatment flexibility. For example, decompression procedures can be performed before or after distracting the adjacent vertebrae at block 2010. Visualization can be used during the decompression procedure to visually identify targeted tissue, as well as ensuring that non-targeted tissue (e.g., nerve tissue) is not traumatized. Although the method is discussed in connection with implanting an interbody fusion implant, the method can be performed to deploy and implant other devices. For example, the method can be used to implant an articulating intervertebral disc. Moreover, the multi-portal systems can be used to implant rigid or fixed interbody fusion devices. The acts and steps in the method of FIG. 19 can be modified based on the features of the implant to perform, for example, an oblique lumbar interbody fusion procedure, a lateral lumbar interbody fusion procedure, a posterior lumbar interbody fusion procedure, a transforaminal lumbar interbody fusion procedure, or an anterior lumbar interbody fusion procedure.

Figure 20:
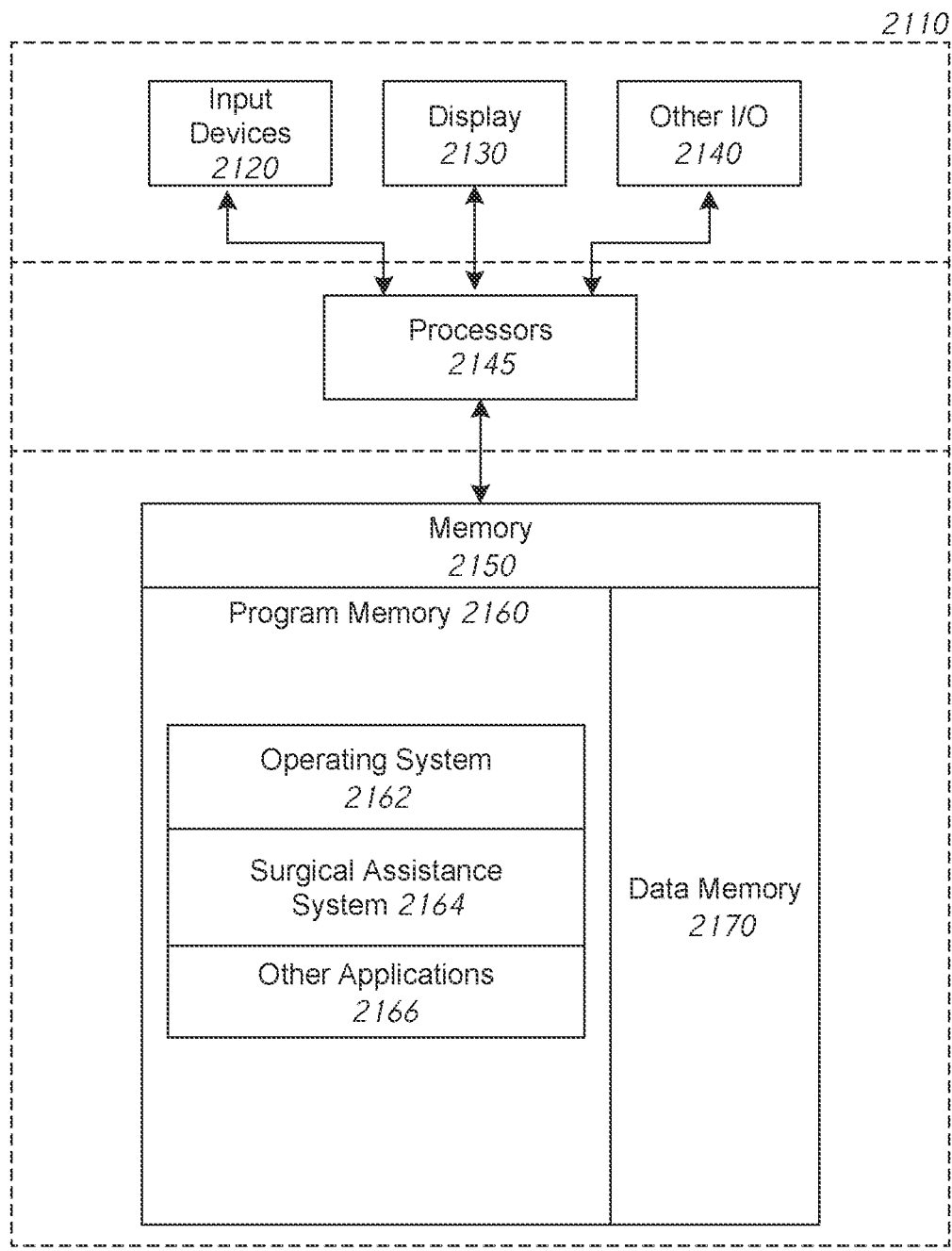
FIG. 20 illustrates a system for providing surgical assistance according to an embodiment of the disclosure.

FIG. 20 illustrates a system 2110 for providing surgical assistance according to an embodiment of the disclosure. The system 2110 can be incorporated into or part of the visualization assembly 160 of FIG. 1. The system 2110 can improve surgeries by displaying image data, analyzing image data, suggesting steps in a surgical procedure, analyzing implants, or the like. The system 2110 can comprise hardware components that improve surgeries using, for example, a surgical assistance system 2164. In various implementations, the surgical assistance system 2164 can store patient information, obtain image data, analyze information/data to obtain results, and use the results to provide feedback to a user. The surgical assistance system 2164 can analyze still images or video from input devices 2120 (e.g., visualization device 2120) to suggest tissue to removed, implants, or surgical steps. For example, the surgical assistance system 2164 can recommend kits (including kit designs), tissue to be removed, surgical paths, surgical steps, and/or the number, size, and configuration of cannulas, instruments, and/or implants. Based on the recommendations, the surgical assistance system 2164 can further suggest surgical instruments, a surgical plan, and other information. The surgical assistance system 2164 can generate a surgical plan including (1) surgical steps, (2) number, size, and/or position of ports/cannulas, and/or (3) surgical approaches. For example, the surgical assistance system 2164 can annotate an image (e.g., an X-ray image, still image, video, etc.) with suggested insertion points along the subject's skin, surgical procedures (e.g., PLIF, ALIF, LLIF, etc.), access paths, etc. During a procedure, the surgical assistance system 1164 can provide warnings or other feedback to surgeons.

System 2110 can include one or more input devices 2120 that provide input to the processor(s) 2145 (e.g., CPU(s), GPU(s), HPU(s), etc.), notifying it of actions. The actions can be mediated by a hardware controller that interprets the signals received from the input device and communicates the information to the processors 2145 using a communication protocol. The processors 2145 can be used to analyze data, such as image data, to determine whether the expanded interbody fusion implant is located at a deployment position based on a position of the expanded interbody fusion implant shown in an acquired image.

Input devices 2120 can include, for example, visualization devices, such as the visualization devices 140, endoscopic instruments, imaging devices (e.g., cameras), CRT machines, X-ray machines, or the like. The visualization, in some surgical embodiments, enables surgeons to visually see and verify the vertebral bodies, vertebral spacing, damaged/displaced tissue, intervertebral discs (including bulging portions), presence of unwanted cartilage (e.g., cartilage buildup), bone, or tissue that is causing nerve root compression and damage to normal body functions. This information on the unwanted material can be documented and recorded by saving image data into a computer database and printing color images (e.g., pictures) immediately for reference and recording. The physician can use the information to develop at least a portion of a surgical plan.

Additionally or alternatively, the input devices 2120 can include a mouse, a keyboard, a touchscreen, an infrared sensor, a touchpad, a wearable input device, a camera- or image-based input device, a microphone, or other user input devices. For example, a mouse can be used to select or manipulate image data captured by visualization devices. A keyboard can be used to annotate image data. The number and configuration of the input devices can be selected based on the physician.

Processors 2145 can be a single processing unit or multiple processing units in a device or distributed across multiple devices. Processors 2145 can be coupled to other hardware devices, for example, with the use of a bus, such as a PCI bus or SCSI bus. The processors 2145 can communicate with a hardware controller for devices, such as for a display 2130. The display 2130 can be used to display image data. For example, the display 2130 can correspond to the display 162 in FIG. 1, which can be connected to one or more visualization devices via a wired or wireless connection (FIG. 1 shows a wired connection). The display 2130 can present information for viewing by a user. The presented information can include suggested implant information, suggested surgical instruments, information for implanting devices, information for repositioning the interbody fusion implant, information for collapsing the interbody fusion implant, or the like. The information can be overlaid on or inserted into images or video. In some embodiments, the information can be annotations.

The display 2130 can provide graphical and textual visual feedback to a user. In some implementations, the display 2130 includes the input device as part of the display, such as when the input device is a touchscreen or is equipped with an eye direction monitoring system. In some implementations, the display is separate from the input device. Examples of display devices are an LCD display screen, a light-emitting diode (LED) display screen, a projected, holographic, or augmented reality display (such as a heads-up display device or a head-mounted device), and so on. The display 2130 can provide high-definition visualization.

Other I/O devices 2140 can also be coupled to the processor, such as a network card, video card, audio card, USB, firewire or other external device, camera, printer, speakers, CD-ROM drive, DVD drive, disk drive, or Blu-Ray device. Other I/O 1140 can also include input ports for information from directly connected medical equipment such as MRI machines, X-ray machines, etc. Other I/O 1140 can further include input ports for receiving data from these types of machines from other sources, such as across a network or from previously captured data, e.g., stored in a database.

The system 2110 can also include a communication device capable of communicating wirelessly or wire-based with a network node. The communication device can communicate with another device or a server through a network using, for example, TCP/IP protocols. The system 2110 can utilize the communication device to distribute operations across multiple network devices.

The processors 2145 can have access to a memory 2150 in a device or distributed across multiple devices. A memory includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. Memory 2150 can include program memory 2160 that stores programs and software, such as an operating system 2162, surgical assistance system 2164, and other application programs 2166. Memory 2150 can also include data memory 2170 that can include, e.g., implantation site information (e.g., level information, implant deployment information, etc.), surgical plan data, user options or preferences, image data, etc., which can be provided to the program memory 2160 or any element of the system 2110.

Some implementations can be operational with numerous other computing systems, environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

The foregoing detailed description has set forth various embodiments of the devices and/or processes via the use of block diagrams, flowcharts, and/or examples. Insofar as such block diagrams, flowcharts, and/or examples containing one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type of medium such as a floppy disc, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Features from various systems, methods and instruments can be combined with features disclosed in U.S. application Ser. No. 15/793,950; U.S. application Ser. No. 17/902,685; U.S. Pat. Nos. 8,632,594; 9,308,099; 10,105,238; 10,201,431; 10,898,340; 11,464,648, PCT App. No. PCT/US20/49982; and PCT App. No. PCT/US22/21193; which are hereby incorporated by reference and made a part of this application. Variations of the implants are contemplated. For example, the interbody spacer 910 (FIGS. 9A-9C) may be provided with different overall heights covering a range of intervertebral disc heights. In other examples, the interbody spacer 910 may be provided with different lordotic and/or kyphotic angles. In still other examples, the interbody spacer 910 may be provided with other patterns or features, such as spikes, protrusions, or the like on the bone contacting surfaces that provide stability and/or resistance to shifting positions. The implant may be made from metal, polymer, ceramic, composite, or other biocompatible and sterilizable material. Different materials may be combined in what is described herein as a single part.

Systems, components, and instruments disclosed herein can be disposable or reusable. For example, the ports, instruments, or cannulas can be disposable to prevent cross-contamination. As used herein, the term "disposable" when applied to a system or component (or combination of components), such as an instrument, a tool, or a distal tip or a head, is a broad term and generally means, without limitation, that the system or component in question is used a finite number of times and is then discarded. Some disposable components are used only once and are then discarded. In other embodiments, the components and instruments are non-disposable and can be used any number of times. In some kits, all of the components can be disposable to prevent cross-contamination. In some other kits, components (e.g., all or some of the components) can be reusable.

Where the context permits, singular or plural terms may also include the plural or singular term, respectively. Moreover, unless the word 'or' is expressly limited to mean only a single item exclusive from the other items in reference to a list of two or more items, then the use of 'or' in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the present technology. Accordingly, the disclosure and

What is claimed is:

1. A multi-portal method for treating a subject's spine, the method comprising:
    inserting a first distal end of a first split cannula into a first entrance formed in a subject, wherein the first split cannula includes a first proximal end with a first flange configured to contact the subject's skin;
    inserting a second distal end of a second split cannula into a second entrance formed in the subject, wherein the second entrance is spaced apart from the first entrance, wherein the second split cannula includes a second proximal end with a second flange configured to contact the subject's skin; and
    manipulating tissue at a target site in the subject using a distal end of an instrument positioned along a first passage of the first split cannula while viewing the tissue and the distal end of the instrument using a visualization instrument positioned along a second passage of the second split cannula.

2. The multi-portal method of claim 1, further comprising:
    incising the subject's tissue to form the first and second entrances on the same side of the subject's midsagittal plane.

3. The multi-portal method of claim 1, wherein the first and second entrances are elongated incisions generally equidistant from and aligned with the subject's midsagittal plane.

4. The multi-portal method of claim 1, wherein a transverse plane of the subject passes through a target site in the subject, wherein the first and second entrances are position on either side of the transverse plane.

5. The multi-portal method of claim 1, wherein the first and second entrances are two spaced apart sagittal incisions.

6. The multi-portal method of claim 1, wherein at least one of the first split cannula or the second split cannula has a length shorter than a distance from the respective first or second entrances to a target site along vertebrae of the spine.

7. The multi-portal method of claim 1, further comprising:
    positioning an open side of the first split cannula to face toward the subject's midsagittal plane; and
    moving a distal portion of the instrument out of a longitudinally-extending opening of the first split cannula to manipulate the tissue at the target site while tissue on opposite sides of the first entrance holds the first split cannula.

8. The multi-portal method of claim 1, wherein at least one of the first split cannula or the second split cannula includes an open side and atraumatic rounded edges extending along the open side and between the first distal end and the first proximal end, wherein the atraumatic rounded edges are configured to tearlessly tension the subject's skin across the open side.

9. The multi-portal method of claim 1, wherein the subject's skin holds the instrument in the first passageway of the first cannula while the tissue is manipulated.

10. The multi-portal method of claim 1, further comprising:
    intra-operatively imaging at least a portion of a spine of the subject;
    selecting the first split cannula from of set of instrument cannulas having different sizes based on the intra-operatively imaging; and
    intra-operatively imaging the first split cannula positioned in the subject prior to manipulating the tissue with the instrument.

11. The multi-portal method of claim 1, further comprising positioning the first and the second split cannulas to direct longitudinal axes of the first and second split cannulas toward a vertebral level along the subject's spine.

12. The multi-portal method of claim 1, further comprising:
    sequentially moving additional instruments along the first passage to manipulate tissue within the subject while the first split cannula is generally positioned between the instrument and non-targeted tissue.

13. The multi-portal method of claim 1, further comprising:
    multi-modality imaging of the target site by concurrently
        (a) intra-operatively imaging, using an external imaging device, the first split cannula and the instrument; and
        (b) viewing the instrument inside the subject using the visualization instrument.

14. The multi-portal method of claim 13, wherein the intra-operatively imaging includes fluoroscopy imaging displayed via a digital screen.

15. The multi-portal method of claim 1, further comprising positioning a port body of the first split cannula in an opening of the first entrance, wherein the port body connects the flange to a split thin-walled shaft of the first split cannula.

16. The multi-portal method of claim 1, further comprising:
    incising the subject's tissue to form the first and second entrances, wherein the first and second entrances are positioned on opposite sides of the subject's midsagittal plane.

17. A multi-portal method for treating a subject, the method comprising:
    inserting a visualization instrument into a first entrance formed in the subject;
    inserting a distal end of a split cannula into a second entrance formed in the subject, wherein the second entrance is spaced apart from the first entrance, wherein the split cannula includes a proximal end with a flange configured to contact the subject's skin when the split cannula is positioned in the second entrance; and
    manipulating tissue at a target site in the subject using a distal end of a surgical instrument positioned along a passage of the split cannula while viewing the tissue and the distal end of the surgical instrument using the visualization instrument extending through the first entrance.

18. The multi-portal method of claim 17, wherein the split cannula has a U-shaped body and motion inhibitors spaced apart from one another along opposing edges of the U-shaped body.

19. The multi-portal method of claim 17, wherein the visualization instrument is spaced apart from and independently movable relative to the surgical instrument manipulating the tissue.

20. The multi-portal method of claim 17, further comprising:
    incising the subject's tissue to form the first and second entrances on the same side of the subject's midsagittal plane.

21. The multi-portal method of claim 17, wherein the first and second entrances are elongated incisions generally equidistant from and aligned with the subject's midsagittal plane.

22. The multi-portal method of claim 17, wherein a transverse plane of the subject passes through the target site, wherein the first and second entrances are position on either side of the transverse plane.

23. The multi-portal method of claim 17, further comprising flushing tissue from the target site using liquid pumped through the visualization instrument.

24. The multi-portal method of claim 17, wherein manipulating the tissue includes at least one of cutting tissue, abrading tissue, or removing tissue.

25. The multi-portal method of claim 17, further comprising sequentially delivering additional surgical instruments into the subject via the split cannula while the visualization instrument is positioned in the subject.

26. The multi-portal method of claim 17, wherein tissue of the subject is movable into the passage of the split cannula while the visualization instrument irrigates target site.

27. A multi-portal method for treating a subject's spine, the method comprising:

inserting a visualization instrument into a first entrance in a subject;

inserting an open-channel split cannula into a second entrance in the subject, wherein the second entrance is separate from the first entrance, wherein the split cannula includes a flange configured to contact the subject's skin; and manipulating tissue at a target site in the subject using at least one instrument positioned along the open-channel split cannula while viewing the target site and the at least one instrument using the visualization instrument positioned through the first entrance.

28. The multi-portal method of claim 27, wherein the open-channel split cannula has a U-shaped body and motion inhibitors spaced apart from one another along opposing edges of the U-shaped body.

29. The multi-portal method of claim 27, wherein the visualization instrument is spaced apart from and independently movable relative to the at least one instrument manipulating the tissue.

\* \* \* \* \*